(12) United States Patent
Krishnamurthy et al.

(10) Patent No.: US 8,124,743 B2
(45) Date of Patent: Feb. 28, 2012

(54) PURIFICATION OF A BIVALENTLY ACTIVE ANTIBODY USING A NON-CHROMATOGRAPHIC METHOD

(75) Inventors: Vijay M. Krishnamurthy, Cambridge, MA (US); Lara A. Estroff, Dryden, NY (US); Vincent Semetey, Paris (FR); Samuel W. Thomas, Boston, MA (US); George K. Kaufman, Somerville, MA (US); Zihni Basar Bilgicer, Cambridge, MA (US); George M. Whitesides, Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 235 days.

(21) Appl. No.: 12/303,089

(22) PCT Filed: Jun. 1, 2007

(86) PCT No.: PCT/US2007/012989
§ 371 (c)(1),
(2), (4) Date: Dec. 1, 2008

(87) PCT Pub. No.: WO2007/143121
PCT Pub. Date: Dec. 13, 2007

(65) Prior Publication Data
US 2009/0240040 A1    Sep. 24, 2009

Related U.S. Application Data

(60) Provisional application No. 60/810,488, filed on Jun. 1, 2006.

(51) Int. Cl.
*C07K 16/00* (2006.01)
*C07K 1/22* (2006.01)
*C07K 1/30* (2006.01)

(52) U.S. Cl. .............. 530/388.9; 424/175.1; 424/177.1; 436/538; 436/539; 436/822; 530/389.8; 530/390.5; 530/413; 530/420

(58) Field of Classification Search ........................ None
See application file for complete search history.

(56) References Cited

U.S. PATENT DOCUMENTS
3,773,919 A    11/1973  Boswell et al.
(Continued)

FOREIGN PATENT DOCUMENTS
DE    3218121    11/1983
(Continued)

OTHER PUBLICATIONS

Carson D. et al. "The separation of rabbit anti-dinitrophenyl IgG antibodies on the basis of combining site depth." Immunochemistry Jul. 1974, vol. 11, No. 7 pp. 355-359.*

(Continued)

*Primary Examiner* — David A Saunders
(74) *Attorney, Agent, or Firm* — Wilmer Cutler Pickering Hale and Dorr LLP

(57) ABSTRACT

The present invention discloses a method of purifying bivalent antibodies or antibody fragments that are active at both Fab sites from a source of antibodies or antibody fragments using a non-chromatographic method that includes inducing the formation of cyclic immunoglobulin aggregates by addition of multivalent hapten to a salt solution of soluble antibodies or antibody fragments, wherein the multivalent hapten possesses a linker between the two haptens effective to prevent the binding of both haptens of the ligand to the same antibody or antibody fragment.

17 Claims, 10 Drawing Sheets

U.S. PATENT DOCUMENTS

| | | | |
|---|---|---|---|
| 4,120,954 A | 10/1978 | Joseph et al. | |
| 4,485,045 A | 11/1984 | Regen | |
| 4,522,811 A | 6/1985 | Eppstein et al. | |
| 4,544,545 A | 10/1985 | Ryan et al. | |
| 4,760,142 A * | 7/1988 | Primes et al. | 544/287 |
| 4,816,567 A | 3/1989 | Cabilly et al. | |
| 6,630,004 B1 | 10/2003 | Philippe et al. | |
| 2005/0271654 A1 | 12/2005 | Rinderknecht et al. | |

FOREIGN PATENT DOCUMENTS

| | | |
|---|---|---|
| EP | 036676 | 9/1981 |
| EP | 052322 | 5/1982 |
| EP | 058481 | 8/1982 |
| EP | 0088046 A2 | 9/1983 |
| EP | 0102324 A2 | 3/1984 |
| EP | 0133988 | 3/1985 |
| EP | 0142641 A2 | 5/1985 |
| EP | 0143949 | 6/1985 |
| EP | 0256190 | 2/1988 |
| JP | 60007934 | 1/1985 |
| WO | WO-97/19106 | 5/1997 |
| WO | WO-03/074148 | 9/2003 |
| WO | WO-03/097587 | 11/2003 |
| WO | WO-2005/073240 | 8/2005 |
| WO | WO-2007/143121 | 12/2007 |
| WO | WO-2008/140595 | 11/2008 |

OTHER PUBLICATIONS

Subramanian Kala et al. "The Fc segment of IgE influences the kinetics of dissociation of a symmetrical bivalent ligand from cyclic dimeric complexes" Biochemistry, vol. 35, No. 17, 1996 pp. 5518-5527.

Wilder R. et al, "Bivalent hapten-antibody interactions—11. Bivalent haptens as probes of combining site depth" Immunochemistry Jan. 1975, vol. 12, No. 1, pp. 49-54.

International Search Report, International Patent Application No. PCT/US07/12989, mailed Nov. 20, 2007 (3 pages).

Ahrer, et al., "Analysis of Aggregates of Human Immunoglobulin G Using Size-Exclusion Chromatography, Static and Dynamic Light Scattering," Journal of Chromatography, A., 1009, 2003, pp. 89-96.

Ahrer, et al., "Thermodynamic Stability and Formation of Aggregates of Human Immunoglobulin G Characterised by Differential Scanning Calorimetry and Dynamic Light Scattering," J. Biochem. Biophys: Methods, 66, 2006, pp. 73-86.

Beck, et al., "Application of Antibodies in the Flow Cytometric Analysis of Benign and Malignant Cells," Seminars in Cancer Biology, vol. 1, 1990, pp. 181-188.

Bilgicer, et al., "A Synthetic Trivalent Hapten that Aggregates Anti-2,4,-DNP IgG into Bicyclic Trimers," J. Am. Chem. Soc., 2007, 129, pp. 3722-3728.

Brennan, et al., "Preparation of Bispecific Antibodies by Chemical Recombination of Monoclonal Immunoglobulin $G_1$ Fragments," Science, vol. 229, Jul. 1985, pp. 81-83.

Brodeur, et al., "4. Mouse-Human Myeloma Partners for the Production of Heterohybridomas," Immunology Series, vol. 33, Monoclonal Antibody Production Techniques and Applications, edited by Lawrence B. Schook, Marcel Dekker, Inc., 1987, pp. 51-63.

Bruggemann, et al., "Designer Mice: The Production of Human Antibody Repertoires in Transgenic Animals," Generation of Antibodies by Cell and Gene Immortalization, Year Immunol. Basel, Karger, 1993, vol. 7, pp. 33-40.

Carter, et al., "Research: High Level *Escherichia coli* Expression and Production of a Bivalent Humanized Antibody Fragment," Bio/Technology, vol. 10, Feb. 1992, pp. 163-167.

Chothia, et al., "Canonical Structures for the Hypervariable Regions of Immunoglobulins," J. Mol. Biol., 1987, 196, pp. 901-917.

Clackson, et al., "Making Antibody Fragments Using Phage Display Libraries," Nature, vol. 352, Aug. 1991, pp. 624-628.

Corbell, "A Comparison of Biological and Calorimetric Analyses of Multivalent Glycodendrimer Ligands for Concanavlin A," Tetrahedron: Asymmetry, 11, 2000, pp. 95-111.

Crothers, et al., "The Influence of Polyvalency on the Binding Properties of Antibodies," Immunochemistry, 1972, vol. 9, pp. 341-357.

Dal Maso, et al., "Review: Epidemiology of Non-Hodgkin Lymphomas and Other Haemolymphopoietic Neoplasms in People with AIDS," The Lancet Oncology, vol. 4, Feb. 2003, pp. 110-119.

David et al., "Protein Iodination with Solid State Lactoperoxidase," Biochemistry, vol. 13, No. 5, 1974, pp. 1014-1021.

Dembo, et al., "A Thermodynamic Model of Binding of Flexible Bivalent Haptens to Antibody," Immunochemistry, vol. 15, 1978, pp. 307-313.

Dembo, et al., "Theory of Equilibrium Binding of Symmetric Bivalent Haptens to Cell Surface Antibody: Application to Histamine Release from Basophils[1]," The Journal of Immunology, vol. 121, No. 1, Jul. 1978, pp. 345-353.

Ei-Serag, H., "Hepatocellular Carcinoma: An Epidemiologic View," J. Clin. Gastroenterol, 2002, 35, Suppl. 2, pp. S72-S78.

Endo, Keigo, "Use of Radiolabeled Monoclonal Antibodies for Diagnostic Imaging," Nihon Igaku Hoshasen Gakkai Zasshi (Japan), Nippon Acta Radiologica, 1990, retrieved from http://ir.library.osaka-u.ac.jp/web/JJRS/, pp. 901-909 , abst only.

Eppstein, et al., "Biological Activity of Liposome-Encapsulated Murine Interferon γ is Mediated by a Cell Membrane Receptor," Proc. Natl. Acad. Sci., vol. 82, Jun. 1985, pp. 3688-3692.

Erickson, et al., "Bivalent Ligand Dissociation Kinetics from Receptor-Bound Immunoglobulin E: Evidence for a Time-Dependent Increase in Ligand Rebinding at the Cell Surface," Biochemistry, 1991, 30, pp. 2357-2363.

Fewtrell, et al., "Larger Oligomers of IgE are More Effective than Dimers in Stimulating Rat Basophilic Leukemia Cells," The Journal of Immunology, vol. 125, No. 2, Aug. 1980, pp. 701-710.

Fujii, et al., "Antimetastatic Activities of Synthetic Arg-Gyl-Asp-Ser (RGDS) and Arg-Leu-Asp-Ser (RLDS) Peptide Analogues and Their Inhibitory Mechanisms," Biol. Pharm. Bull. 18(12), 1995, pp. 1681-1688.

Goding, James W., "3. Production of Monoclonal Antibodies," Monoclonal Antibodies: Principles and Practice, Production and Application of Monoclonal Antibodies in Cell Biology, Biochemistry and Immunology, Second Edition, Academic Press, Inc., 1986, pp. 59-103.

Goldenberg, et al., "Biological and Clinical Perspectives of Cancer Imaging and Therapy with Radiolabeled Antibodies," Seminars in Cancer Biology, vol. 1, 1990, pp. 217-225.

Green et al., "Detection of Antibody Monomers, Dimers and Polymers Upon Interaction of a Homologous Series of Divalent Haptens with its Specific Antibody," Biochemical and Biophysical Research Communications, vol. 46, No. 2, 1972, pp. 738-744.

Green et al., "Protein Fractionation on the Basis of Solubility in Aqueous Solutions of Salts and Organic Solvents," Methods Enzymol. 1, 1955, pp. 67-90.

Hermann, et al., "Review Article: Epstein-Barr Virus-Associated Carcinomas: Facts and Fiction," Journal of Pathology, 2003, 199, pp. 140-145.

Hernandez-Avila, et al., "Human Papilloma Virus 16-18 Infection and Cervical Cancer in Mexico: A Case-Control Study," Archives of Medical Research, vol. 28, No. 2, 1997, pp. 265-271.

Hlavacek, et al., "The Complexity of Complexes in Signal Transduction," Biotechnol. Bioeng., Nov. 2003, pp. 783-794.

Hoogenboom, et al., "By-passing Immunisation: Human Antibodies from Synthetic Repertoires of Germline $V_H$ Gene Segments Rearranged in Vitro," J. Mol. Biol., 1992, 227, pp. 381-388.

Hwang, et al., "Hepatic Uptake and Degradation of Unilamellar Sphingomyelin/Cholesterol Liposomes: A Kinetic Study," Proc. Natl. Acad. Sci., vol. 77, No. 7, Jul. 1980, pp. 4030-4034.

International Search Report and Written Opinion of the International Searching Authority, the European Patent Office, for International Application No. PCT/US2007/086163, dated Mar. 25, 2009.

Jakobovits et al., "Analysis of Homozygous Mutant Chimeric Mice: Deletion of the Immunoglobulin Heavy-Chain Joining Region Blocks B-cell Development and Antibody Production," Proc. Natl. Acad. Sco., vol. 90, Mar. 1993, pp. 2551-2555.

Jayaraman, et al., "PII: S0040-4039(97)01548-7, Synthesis of Carbohydrate-Containing Dendrimers. 5. Preparation of Dendrimers Using Unprotected Carbohydrates," Tetrahedron Letters, vol. 38, No. 38, pp. 6767-6770, 1997.

Jones et al., "Replacing the Complementarity-determining Regions in a Human Antibody with Those from a Mouse," Nature, vol. 321, May 1996, pp. 522-525.

Kadow, et al., "The Role of Viruses in Human Cancer Development and Antiviral Approaches for Intervention," Current Opinion in Investigational Drugs, 2002, vol. 3, No. 11, pp. 1574-1579.

Kane, et al., "Cross-Linking of IgE-Receptor Complexes at the Cell Surface: Synthesis and Characterization of a Long Bivalent Hapten that is Capable of Triggering Mast Cells and Rat Basophilic Leukemia Cells," Molecular Immunology, vol. 23, No. 7, pp. 783-790, 1986.

Kita et al., "Contribution of the Surface Free Energy Perturbation to Protein-Solvent Interactions," Biochemistry, 1994, 33, pp. 15178-15189.

Kitov, et al., "On the Nature of the Multivalency Effect: A Thermodynamic Model," J. Am. Chem. Soc., 2003, 125, pp. 16271-16284.

Kohler, et al., "Continuous Cultures of Fused Cells Secreting Antibody of Predefined Specificity," Nature, vol. 256, Aug. 1975, pp. 495-497.

Kozbor, et al., "A Human Hybrid Myeloma for Production of Human Monoclonal Antibodies[1]," The Journal of Immunology, vol. 133, No. 6, Dec. 1984, pp. 3001-3005.

Kreuzer, et al., "Ligand-Dependent Autophosphorylation of the Insulin Receptor is Positively Regulated by $G_i$-proteins," Biochem. J., 2004, 380, pp. 831-836.

Krishnamurthy, et al., "2. Multivalency in Ligand Design," Fragment-Based Approaches in Drug Discovery, Edited by Wolfgang Jahnke and Daniel A. Erlanson, 2006, Wiley-VCH Verlag GmbH & Co., pp. 11-53.

Langer et al, "Biocompatability of Polymeric Delivery Systems for Macromolecules," Journal of Biomedical Materials Research, vol. 15, 1981, pp. 267-277.

Langer, "Controlled Release of Macromolecules," Chemtech, Feb. 1982, pp. 98-105.

Laue, et al., "Modern Applications of Analytical Ultracentrifugation," Annu. Rev. Biophys. Biomol. Struct., 1999, 28, pp. 75-100.

Leung, et al., "Synthesis and Binding Properties of Cyclodextrin Trimers," Tetrahedron Letters, 42, 2001, pp. 6255-6258.

Lou, et al., "Radical Cation Formation in Characterization of Novel C3-symmetric disks and Their Precursors by Matrix-Assisted Laser Desorption/Ionization Time-of-Flight Mass Spectrometry," Journal of Mass Spectrometry, 2006, 41, pp. 659-669.

Luedtke, et al., "Proximity of Antibody Binding Sites Studies by Fluorescence Energy Transfer," Biochemistry, 1980, 19, pp. 1182-1192.

Malbon, C., "G Proteins in Development," Molecular Cell Biology, vol. 6, Sep. 2005, pp. 689-701.

Malbon, "Commentary: Insulin Signalling: Putting the 'G-' in protein-protein interactions," Biochem J., 2004, 380, pp. e-11-e12.

Mammen, et al., "Polyvalent Interactions in Biological Systems: Implications for Design and Use of Multivalent Ligands and Inhibitors," Agnew. Chem. Int. Ed., 1998, 37, pp. 2754-2794, 41 pages.

Marks et al., "By-passing Immunication: Human Antibodies from V-Gene Libraries Displayed on Phage," J. Mol. Biol., 1991, 222, pp. 581-597.

Marks, et al., "Research: By-Passing Immunication: Building High Affinity Human Antibodies by Chain Shuffling," Bio/Technology, vol. 10, Jul. 1992, pp. 779-783.

McCafferty, et al, "Phage Antibodies: Filameritous Phage Displaying Antibody Variable Domains," Nature, vol. 348, Dec. 1990, pp. 552-554.

Morimoto, et al., "Single-step Purification of F(ab')$_2$ Fragments of Mouse Monoclonal Antibodies (immunoglobulins G1) by Hydrophobic Interaction High Performance Liquid Chromatography Using TSKgel Phenyl-5PW," Journal of Biochemical and Biophysical Methods, 24, 1992, pp. 107-117.

Morrison, et al., "Chimeric Human Antibody Moleculees: Mouse Antigen-Binding Domains with Human Constant Region Domains," Proc. Natl. Acad. Sci., vol. 81, Nov. 1984, pp. 6851-6855.

Mortreux, et al., "Review: Molecular and Cellular Aspects of HTLV-1 Associated Leukemogenesis in vivo," Leukemia, 2003, 17, pp. 26-38.

Muller, et al., "Tethering of Long-Chain Amino Acids to a Rigid Aromatic Core-A New Type of Preorganized Surfactants Acting as Flotative Agents," Journal of Surfactants and Detergents, vol. 4, No. 4, Oct. 2001, pp. 407-414.

Munson et al., "LIGAND: A Versatile Computerized Approach for Characterization of Ligand-Binding Systems," Analytical Biochemistry, 107, 1980, pp. 220-239.

Niman, Henry L., "13. Use of Monoclonal Antibodies as Probes for Oncogene Products," Immunodiagnosis of Cancer, Second Edition, Edited by Ronald B. Herberman, Marcel Dekker, Inc., 1990, pp. 189-204.

Nygren, et al., "Conjugation of Horseradish Perosidase to Fab Fragments with Different Homobifunctional and Heterobifunctional Cross-Linking Reagents, a Comparative Study," The Journal of Histochemistry and Cytochemistry, vol. 30, No. 5, 1982, pp. 407-412.

Pain, et al., "Preparation of Protein A-Peroxidase Monoconjugate Using a Heterobifunctional Reagent, and its Use in Enzyme Immunoassays," Journal of Immunological Methods, 40, 1981, pp. 219-230.

Parsegian, "Hopes for Hofmeister," Nature, vol. 378, Nov. 1995, pp. 335-336.

Pedro A. Lehmann F., "Conformations of Highly Hindered Aryl Ethers-XVIII, Neighboring-Ring Anisotropy Effects in Poly(2,4-Dinitrophenoxy)Benzenes[1,2]," Tetrahedron, vol. 30, 1974, pp. 719-726.

Pluckthun, "Mono- and Bivalent Antibody Fragments Produced in *Escherichia coli*: Engineering, Folding and Antigen Binding," Immunological Reviews, 1992, No. 130, pp. 151-188.

Posner, et al., "A Quantitative Approach for Studying IgE-FcεRI Aggregation," Molecular Immunology, 38, 2001, pp. 1221-1228.

Posner, et al., "Dissociation Kinetics of Bivalent Ligand-Immunoglobulin E Aggregates in Solution," Biochemistry, 1991, 30, pp. 2348-2356.

Posner, et al., "The Kinetics of Bivalent Ligand-Bivalent Receptor Aggregation: Ring Formation and the Breakdown of the Equivalent Site Approximation," Mathematical Biosciences, 126, 1995, pp. 171-190.

Presta, et al., "Humanization of an Antibody Directed Against IgE," The Journal of Immunology, vol. 151, No. 5, Sep. 1993, pp. 2623-2632.

Raman, et al., "Enthalpy of Antibody-Cytochrome c Binding," Biochemistry, 1995, 34, pp. 5831-5838.

Raman, et al., "Glycomics: An Integrated Systems Approach to Structure-Function Relationships of Glycans," Nature Methods, vol. 2, No. 11, Nov. 2005, pp. 817-824.

Rao, et al., "A Trivalent System from Vancomycin•D-Ala-D-Ala with Higher Affinity than Avidin•Biotin," Science, vol. 280, May 1998, pp. 708-711.

Rao, et al., "Design, Synthesis, and Characterization of a High-Affinity Trivalent System Derived from Vancomycin and $_L$-Lys-D-Ala-$_D$-Ala," J. Am. Chem. Soc., 2000, 122, pp. 2698-2710.

Rao, et al., "Tight Binding of a Dimeric Derivative of Vancomycin with Dimeric $_L$-Lys-$_D$-Ala-D-Ala," J. Am. Chem. Soc., 1997, 119, pp. 10286-10290.

Reichmann, et al., "Reshaping Human Antibodies for Therapy," Nature, vol. 332, Mar. 1988, pp. 323-327.

Rivas, et al., "New Developments in the Study of Biomolecular Associations via Sendimentation Equilibrium," TIBS, 18, Aug. 1993, pp. 284-287.

Roux, et al., "Comparisons of the Ability of Human IgG3 Hinge Mutants, IgM, IgE, and IgA2, to Form Small Immune Complexes: A Role for Flexibility and Geometry," The Journal of Immunology, 1998, 161, pp. 4083-4090.

Roux, et al., "Flexibility of Human IgG Subclasses[1]," The Journal of Immunology, 1997, 159, pp. 3372-3382.

Rupley, et al., "Water and Globular Proteins," TIBS, Jan. 1983, pp. 18-22.

Sanda, et al., "Feature Article: Syntheses and Functions of Polymers Based on Amino Acids," Macromol. Chem. Phys., 200, No. 12, 1999, pp. 2651-2661.

Schweitzer-Stenner, et al., "Oligomerization and Ring Closure of Immunoglobulin E Class Antibodies by Divalent Haptens," Biochemistry, 1987, 26, pp. 3602-3612.

Sears, et al., "Carbohydrates and Glycobiology Review: Toward Automated Synthesis of Oligosaccharides and Gylcoproteins," Science, vol. 291, Mar. 2001, pp. 2344-2350.

Sidman, et al., "Controlled Release of Macromolecules and Pharmaceuticals from Synthetic Polypeptides Baed on Glutamic Acid," Biopolymers, vol. 22, 1983, pp. 547-556.

Sims, et al., "A Humanized CD18 Antibody Can Block Function without Cell Destruction," The Journal of Immunology, vol. 151, No. 4, Aug. 1993, pp. 2296-2308.

Solomon, et al., "Heterobifunctional Multivalent Inhibitor-Adaptor Mediates Specific Aggregation between Shiga Toxin and a Pentraxin," Organic Letters, 2005, vol. 7, No. 20, pp. 4369-4372.

Strelets, et al., "The Role of the Hinge Region in Human IgG Immune Complex Formation," The FASEB Journal, Abstracts, The Federation of American Societies for Experimental Biology, Apr. 1996, vol. 10, No. 6, pp. 973.

Timasheff, et al., "14. Stabilization of Protein Structure by Solvents," Protein Structure, A Practical Approach, Oxford Press University, T.E. Creighton, ed., 1997, pp. 349-364.

Verhoeyen, et al., "Reshaping Human Antibodies: Grafting an Antilysozyme Activity," Science, vol. 239, Mar. 1988, pp. 1534-1536.

Warner, et al., "Detection of a Conformational Change in an Antihapten-Antibody System Upon Interaction with Divalent Hapten*," Biochemistry, vol. 9, No. 3, Feb. 1970, pp. 451-459.

Warner, et al., "Detection of Two Species of Antibody Molecules with the Same Specificity," Biochemical and Biophysical Research Communications, vol. 41, No. 1, 1970, pp. 225-231.

Waterhouse, et al., "Combinatorial Infection and in vivo Recombination: A Strategy for Making Large Phage Antibody Repertoires," Nucleic Acids Research, 1993, vol. 21, No. 9, pp. 2265-2266.

Whitesides, et al., "Essay: Designing Ligands to Bind Proteins," Quarterly Reviews of Biophysics, 38, 4, 2005, pp. 385-395.

Yang, et al., "Self-Assembled Aggregates of IgGs as Templates for the Growth of Clusters of Gold Nanoparticles," Agnew. Che., 2004, 116, pp. 1581-1584.

Zhang, et al., "Large Cyclic Peptides as Cores of Multivalent Ligands: Application to Inhibitors of Receptor Binding by Cholera Toxin," J. Org. Chem., 2004, 69, pp. 7737-7740.

Zola, "Monoclonal Antibodies: A Manual of Techniques," CRC Press, Inc., 1987, pp. 147-181, 37 pages.

Carter, et al., "Humanization of an Anti-p185$^{HER2}$ Antibody for Human Cancer Therapy," Proc. Natl. Acad. Sci., vol. 89, May 1992, Immunology, pp. 4285-4289.

Hunter, et al., Preparation of Iodine-131 Labelled Human Growth Hormone of High Specific Activity, Nature, vol. 194, May 1962, pp. 495-496.

Jakobovits, et al., "Germ-line Transmission and Expression of a Human-Derived Yeast Artificial Chromosome," Letters to Nature, Nature, vol. 362, Mar. 1993, pp. 255-258.

Muller, et al., "Novel Amphiphiles with Preorganized Functionalities-Formation of Lamgmuir-Films and Efficiency in Mineral Flotation," Advances in Colloid and Interface Science 114-115, 2005, pp. 291-302.

Presta, "Antibody Engineering," Current Opinion in Structural Biology, Engineering and Design, 1992, 2:593-596.

Skerra, "Bacterial Expression of Immunoglobulin Fragments," Current Opinion in Immunology, 1993, vol. 5: 256-262.

Sun, et al., "Thermodynamic Studies on the Recognition of Flexible Peptides by Transition-Metal Complexes," Inorganic Chemistry Article, vol. 41, No. 6, 2002, pp. 1584-1590.

* cited by examiner

US 8,124,743 B2

PURIFICATION OF A BIVALENTLY ACTIVE ANTIBODY USING A NON-CHROMATOGRAPHIC METHOD

RELATED APPLICATIONS

This application claims the benefit of U.S. Provisional Application No. 60/810,488, filed Jun. 1, 2006, hereby incorporated by reference in its entirety.

This invention was made with government support under EB003361 and GM030367 awarded by the National Institutes of Health. The government has certain rights in the invention.

FIELD OF THE INVENTION

This invention relates generally to antibody purification. In particular, the invention relates to a method for isolating an antibody or an antibody fragment from impurities and contaminants associated therewith.

DESCRIPTION OF THE RELATED ART

Numerous studies have disclosed antibody purification schemes involving the use of gel electrophoresis, dialysis and chromatography (i.e., ion-exchange, gel filtration, hydroxylapatite chromatography, and affinity chromatography in particular).

In Green, G. et al. 1972 Biochem and Biophys Res Comm 46:738-744, the investigators varied the linker length of bivalent DNP haptens and bound these to polyclonal, purified IgGs. They examined speciation of IgG into dimer and polymer by analytical ultracentrifugation. They began with a heterogeneous starting pool (polyclonal IgG) and rationalized that the different distribution of IgG aggregates was due to different depths of the combining sites (Fab sites) for the different IgGs.

In Warner, C. and Schumaker, V. 1970 Biochem and Biophys Res Comm 41:225-231, the investigators incubated purified anti-DNP polyclonal IgG with a bivalent hapten and separated monomer and dimer IgG fractions using size-exclusion chromatography. They dissociated IgG dimer with dinitrophenol.

In Warner, C. and Schumaker, V. 1970 Biochemistry 9:451-459, the investigators showed that the IgG dimer fraction separated by size exclusion chromatography was stable for greater than 2 months.

Carson and Metzger performed a similar study but they varied the length of the linker in the bivalent hapten (Carson, D and Metzger, H. 1974 Immunochemistry 11:355-359. They separated purified polyclonal IgG dimers and monomers using size exclusion chromatography. They also examined the dimerization of Fab regions with bivalent haptens, and determined that the amount of dimerization of IgGs was the same as for the component Fabs (and could relate to the depth of the combining site of the Fab).

Wilder, R. L. et al. 1975 Immunochemistry 12:49-54 examined the binding of bivalent haptens to (Fab)$_2$ proteins (as well as IgG and Fab). The authors speculated that IgG antibodies could be separated based on combining site depth (ability to form dimeric aggregates with bivalent haptens of different linker lengths).

Schweitzer-Stenner, R. et al. 1987 Biochemistry 26:3602-3612 examined the binding of monoclonal anti-DNP IgE to bivalent haptens with oligoproline linkers of varying length (there was an intermediate length where IgG dimers/trimers predominated; bivalent haptens with shorter and longer linkers gave largely IgG monomer). They fit the data to a model that suggested that with very long bivalent haptens, both Fab sites of the IgG were bound to the same bivalent hapten.

Subramanian, K. et al. 1996 Biochemistry 35:5518-5527 demonstrated that monoclonal anti-DNP IgE dimers and monomers (formed by incubation with bivalent hapten) could be separated by size exclusion chromatography.

SUMMARY OF THE INVENTION

The present invention discloses a method of purifying bivalent antibodies or antibody fragments that are active at both Fab sites from a source of antibodies or antibody fragments using a non-chromatographic method that includes inducing the formation of cyclic immunoglobulin aggregates by addition of bivalent hapten to a salt solution of soluble antibodies or antibody fragments, wherein the bivalent hapten possesses a linker between the two haptens effective to prevent the binding of both haptens of the ligand to the same antibody or antibody fragment.

A second embodiment of the invention relates to a method of purifying bivalent antibodies or antibody fragments that are active at both Fab sites from a source of antibodies or antibody fragments using a non-chromatographic method that includes:

(a) removing high molecular weight proteins by salt precipitation and recovery of antibody or antibody fragment that remains soluble, and (b) inducing the formation of cyclic immunoglobulin aggregates by addition of bivalent hapten to the supernatant from (a), wherein the bivalent hapten possesses a linker between the two haptens effective to prevent the binding of both haptens of the ligand to the same antibody or antibody fragment.

A third embodiment of the invention relates to a method of purifying bivalent antibodies or antibody fragments that are active at both Fab sites from a source of antibodies or antibody fragments using a non-chromatographic method that includes:

(a) removing high molecular weight proteins by salt precipitation and recovery of antibody or antibody fragment that remains soluble, (b) inducing the formation of cyclic immunoglobulin aggregates by addition of bivalent hapten to the supernatant from (a), wherein the bivalent hapten possesses a linker between the two haptens effective to prevent the binding of both haptens of the ligand to the same antibody or antibody fragment, and (c) dissolving cyclic immunoglobulin aggregates recovered from (b) and dissociating them from bivalent hapten by addition of excess monovalent hapten.

A fourth embodiment of the invention relates to a method of purifying bivalent antibodies or antibody fragments that are active at both Fab sites from a source of antibodies or antibody fragments using a non-chromatographic method that includes:

(a) removing high molecular weight proteins by salt precipitation and recovery of antibody or antibody fragment that remains soluble, (b) inducing the formation of cyclic immunoglobulin aggregates by addition of bivalent hapten to the supernatant from (a), wherein the bivalent hapten possesses a linker between the two haptens effective to prevent the binding of both haptens of the ligand to the same antibody or antibody fragment, (c) dissolving cyclic immunoglobulin aggregates recovered from (b) and dissociating them from bivalent hapten by addition of excess monovalent hapten, and (d) dialyzing the antibodies or antibody fragments to remove the monovalent haptens.

DETAILED DESCRIPTION OF THE PREFERRED EMBODIMENT

This disclosure describes the development of a procedure for the purification of a bivalently active antibody using a non-chromatographic method. This procedure is based on the formation and isolation of discrete cyclic aggregates of antibodies in the presence of synthetic, bi and trivalent haptens. Salt precipitation of cyclic IgG aggregates, which are formed by reaction of antibody with bi and trivalent haptens, can separate bivalently active antibody from monovalently active antibodies and other contaminants in the source without the need for any chromatographic steps.

In one embodiment, this paper describes the development of a four-step procedure for the purification of a model monoclonal antibody (rat anti-2,4-dinitrophenyl IgG, $IgG^{DNP}$) from ascites fluid. This procedure is based on the formation and isolation of discrete cyclic aggregates of antibodies in the presence of synthetic bi and trivalent haptens. Ammonium sulfate precipitation of IgG aggregates, which are formed on reaction of $IgG^{DNP}$ with bivalent haptens and trivalent haptens of 2,4-dinitrophenyl (2,4-DNP) and 4-nitrophenyl (4-NP) molecules, can separate bivalently active antibody from monovalently active antibodies, and from other proteins and globulins in ascites fluid, without the need for chromatographic steps. The $IgG^{DNP}$ has a monovalent Kd of 8 nM for 2,4-DNP and a monovalent Kd of ~0.5 µM for 4-NP. We demonstrated that multivalent versions of both 2,4-DNP and 4-NP were equivalently effective for purification of $IgG^{DNP}$ from ascites fluid. From 0.5 mL of ascites fluid, we isolated 0.8 mg of bivalently active anti-2,4-DNP. The purity of the isolated IgG was >90%, based on size exclusion chromatography (SE-HPLC) when a constant molar absorptivity at 214 nm was assumed for all species.

The technique has two advantages over other techniques for the purification of antibodies: i) the isolated material is guaranteed to have two fully active Fab binding sites, because both sites are required to form the cyclic aggregates; ii) the procedure does not require chromatographic separation. It has a limitation over the standard procedures in that the hapten must have a structure that is compatible with synthesis of bi and/or trivalent analogs.

Figure 1:
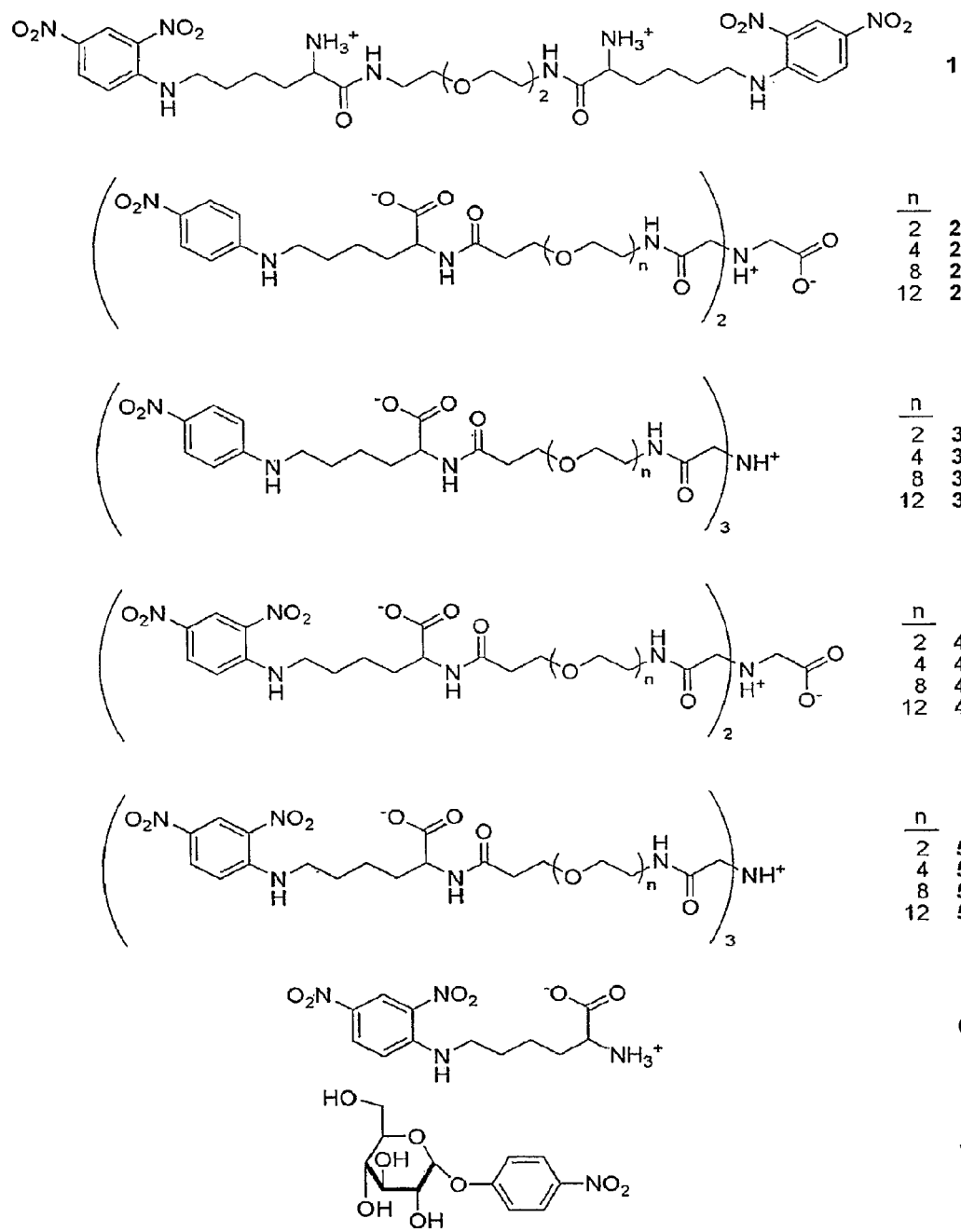
FIG. 1. Structures of the di and trivalent hapten molecules (1, 2a-2d, 3a-3d, 4a-4d, and 5a-5d) and monovalent (6) 2,4-dinitrophenyl lysine, and the 4-nitrophenyl derivative, 7, used in this study.

One embodiment of the invention is the development of a method for the facile purification of monoclonal antibodies (mAbs), which are active at both Fab sites (bivalently active), from ascites fluid using a model IgG (rat anti-2,4-dinitrophenyl). The purification procedure is based on the formation of soluble, stable aggregates by interaction of the antibody with di and trivalent haptens, followed by ammonium sulfate precipitation of these aggregates (FIG. 1). This precipitation separates the antibody aggregates from other antibodies that do not form aggregates, and from other serum proteins in the ascites fluid. To the best of our knowledge, this technique is the first purification procedure for monoclonal IgGs that ensures the product is bivalently active.

Why are Bivalently Active Antibodies Important?

Monoclonal antibodies have become increasingly important for biomedical research and as clinical therapeutics. Key to the function of antibodies in vivo is their multivalent nature: the basic immunoglobulin structure is bivalent (FIG. 2a). IgG and IgE antibodies have only one bivalent unit, while IgA and IgM consist of multiple bivalent units and thus have higher valencies (4 and 10, respectively). This bivalency increases the avidity of antibodies for cell surfaces displaying antigens as well as for soluble, multivalent antigens and allergens. There are several complications that can produce monoclonal antibodies with only one active Fab binding site; examples include protein misfolding events, heat or chemical damage, and the "scrambling" of light chains. The lack of sufficient quantities of mAbs that are homogenously bivalently active has made it difficult to establish rigorously the consequences of bivalency in the immune system. For example, it is unknown what density of antigens on the surface of a pathogen is required for an antibody (with a given affinity) to bind tightly enough to trigger an immune response. Our primary motivation in developing the purification procedure reported here was to generate mAbs in milligram quantities, in which we were confident that both Fab binding sites were active for physical-organic studies of the mechanisms of oligovalency in immunology.

Commonly Used Purification Methods for Monoclonal Antibodies do not Guarantee Bivalent Antibody Current procedures for purifying antibodies rely heavily on affinity techniques but do not distinguish between mono- and bivalently active species. Two general approaches are commonly used to purify monoclonal antibodies:

1) One approach purifies antibodies based upon their common structural characteristics (size, charge, Fc region, etc). The first step in these procedures is precipitation of the antibodies by the addition of ammonium sulfate (to a final concentration 45% of the maximum solubility of the salt at 4° C.; referred to below as a 45% ammonium sulfate solution) to ascites fluid. After solubilization of the resulting pellet, the antibody is then further purified by one or more different types of chromatographies: Fc affinity chromatography (Protein A or Protein G), ion-exchange chromatography, hydroxyapatite chromatography, or size-exclusion chromatography (SEC). Proteins A and G only bind to the Fc region of antibodies (with varying affinities depending on the isotype and species of origin) and SEC only purifies antibody based on size (correlated with molecular weight). Antibody is removed from Protein A/G columns by dissociation at low pH (~3.5)- conditions under which some antibodies denature.

2) The second approach purifies antibodies based upon activity of the Fab binding sites. This technique requires affinity chromatography with resin functionalized with antigen or small molecule hapten. Typically, antibody is eluted using gradients in either pH or ionic strength. By eluting with a gradient of competing soluble hapten, the antibody could theoretically be fractionated according to avidity. Such an approach could possibly separate monovalently active antibody from divalently active antibody. The affinity ($K_d^{mono}$) and avidity ($K_d^{di}$) of antibodies usually differ by no more than a factor of $10^2$; this small factor makes such a separation strategy challenging. Monoclonal antibodies for human therapeutics require additional filtration and chromatography steps to remove viruses and endotoxins, respectively. For example, depyrogenated resins (e.g., polimyxin B-Sepharose or Actigel ALD) are used to remove endotoxins.

Disadvantages of Current Purification Techniques for Monoclonal Antibodies

There are several disadvantages to current purification procedures. Chromatographic approaches, such as those described above, are labor-intensive, expensive, and operationally demanding at large scales. Most importantly, techniques based on affinity chromatography towards either Fc or Fab sites do not ensure homogeneous, bivalently active antibodies: such techniques only require an intact Fc region or one active Fab region of high affinity (Kd~nM) to isolate antibodies. The technique introduced here is based on the formation of discrete, cyclic aggregates of antibodies, and therefore has the potential to avoid many of these disadvantages. Importantly, this purification procedure differs from conventional techniques in that it requires both Fab sites of an antibody to be active.

Formation of Cyclic Aggregates of Antibodies

Early in the development of molecular immunology, investigators described the formation of discrete, cyclic dimers and trimers resulting from the aggregation of IgE's and IgG's with bivalent haptens (FIG. 2b). Based on analytical modeling of the assembly of antibody aggregates, other investigators predicted that the maximum amount of aggregate that can be formed would depend on the monovalent binding constant ($K_d^{affinity}$) of the antibody for the hapten—the tighter the antibody-hapten interaction (the lower the value of $K_d^{affinity}$), the higher the conversion of antibody to aggregates. Their theoretical work also predicted that the divalent hapten concentration ($C_{total}$) at which maximum conversion ($C_{Tmax}$) would be observed would depend on the monovalent dissociation constant and the total concentration of antibody ($[IgG]_{total}$) as shown in eq 1:

$$C_{Tmax} = K_d^{affinity}/2 + [IgG]_{total} \quad (1)$$

We used these predictions from this model, along with the experimental work of others to design our experiments.

Experimental Design

Purification Procedure

Figure 4:
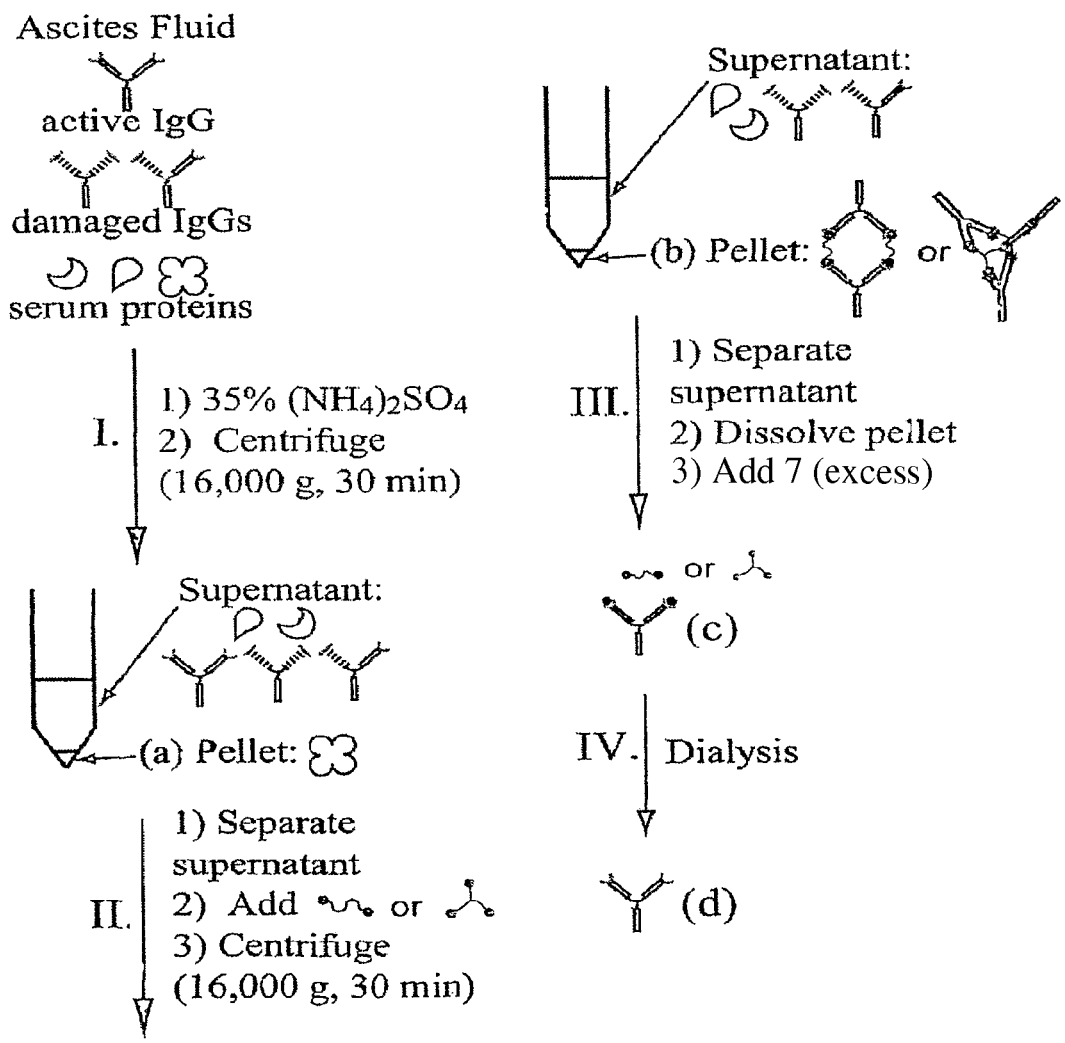
FIG. 4. A schematic representation of the four steps (I-IV) used to purify bivalently active monoclonal anti-DNP IgG from ascites fluid using ammonium sulfate precipitation. The starting material is ascites fluid, which contains a mixture of: IgG with two active Fab binding sites that both recognize 2,4-DNP (active IgG), improperly folded or denatured anti-2,4-DNP IgG (damaged IgG), and IgG fragments (heavy or light chain) and contaminant proteins (serum proteins) with a range of molecular weights. (I) Low ammonium sulfate (35%) precipitates high molecular weight (>300 kDa) proteins that are separated by centrifugation as pellet (a). The supernatant, which contains all IgG and low molecular weight serum proteins, is carried on. (II) The addition of bi or trivalent antigen to the supernatant forms aggregates of IgG (represented here as cyclic dimer, and bicyclic trimer FIG. 2b), which immediately precipitate from the solution. This pellet (b) is isolated by centrifugation from the supernatant, which now contains the monovalent damaged IgG and other serum proteins. (III) The pellet (b) is re-dissolved and the IgG aggregates are dissociated by the addition of excess monovalent antigen 7 (~1 mM). (IV) Dialysis against excess 7 (to prevent the re-formation of IgG aggregates) and then against phosphate buffered saline (pH 7.4) gives the final product: monomeric, bivalently active, IgG antibody. The recovered activity from ELISA was ~10% of the starting activity in the ascites fluid.

We report the purification process from ascites fluid; ascites fluid and the supernatant from hybridoma bio-reactors are the two most common biological sources for monoclonal antibodies for both small and large scales. Ascites fluid contains 1-10 mg/mL of globulins, and high concentrations of other serum proteins including albumin (MW~66 kD) and transferrin (MW~80 kD). In one embodiment, this purification procedure uses four steps to generate purified bivalently active anti-2,4-DNP from rat ascites fluid (FIG. 4). After removing high molecular-weight contaminants from the ascites fluid by precipitating them with ammonium sulfate (FIG. 4a), we induce the formation of aggregates (e.g., dimers, trimers, and tetramers) of IgG by incubation with a bi or trivalent hapten (FIG. 4b). These aggregates immediately precipitate in the 35% AMS solution, and are isolated by centrifugation (FIG. 4b). The supernatant, which contains IgG incapable of forming aggregates with multivalent haptens (i.e., one or no Fab sites), and lower molecular weight serum proteins, is discarded. We re-suspend the pellet and dissociate the aggregates by incubation with a large excess of monovalent hapten (FIG. 4c). Exhaustive dialysis removes the low molecular weight haptens (FIG. 4d). The final product is purified anti-2,4-DNP IgG with two active Fab binding sites.

Antibody and Hapten Selection

We chose anti-2,4-DNP monoclonal IgG1κ antibody (from clone LO-DNP-2) for a proof-of-principle demonstration for the following reasons: (i) the purified antibody and the ascites fluid are both commercially available (Technopharm, France), (ii) the antibody has a high affinity (low $K_d$=~8 nM) for monovalent DNP (a requirement to observe and isolate the aggregates by SE-HPLC), and weaker affinity ($K_d$=~0.5 μM) for monovalent 4-N-P (which we use to demonstrate the range $K_d$ for applicability of our procedure), and (iii) the synthesis of bi and trivalent 4-NP and 2,4-DNP haptens (e.g., 1) are straightforward.

Analytical Method Selection

We used size-exclusion chromatography (SE-HPLC) to follow the purification process. This analytical technique has the advantage that we can resolve monomeric, dimeric, trimeric, and tetrameric antibody aggregates on the column. It has the disadvantage that these aggregates must be kinetically stable (in the absence of competing monovalent hapten) over the time required to carry out a separation (retention time, tr~15 min).

Results and Discussion

Figure 2:
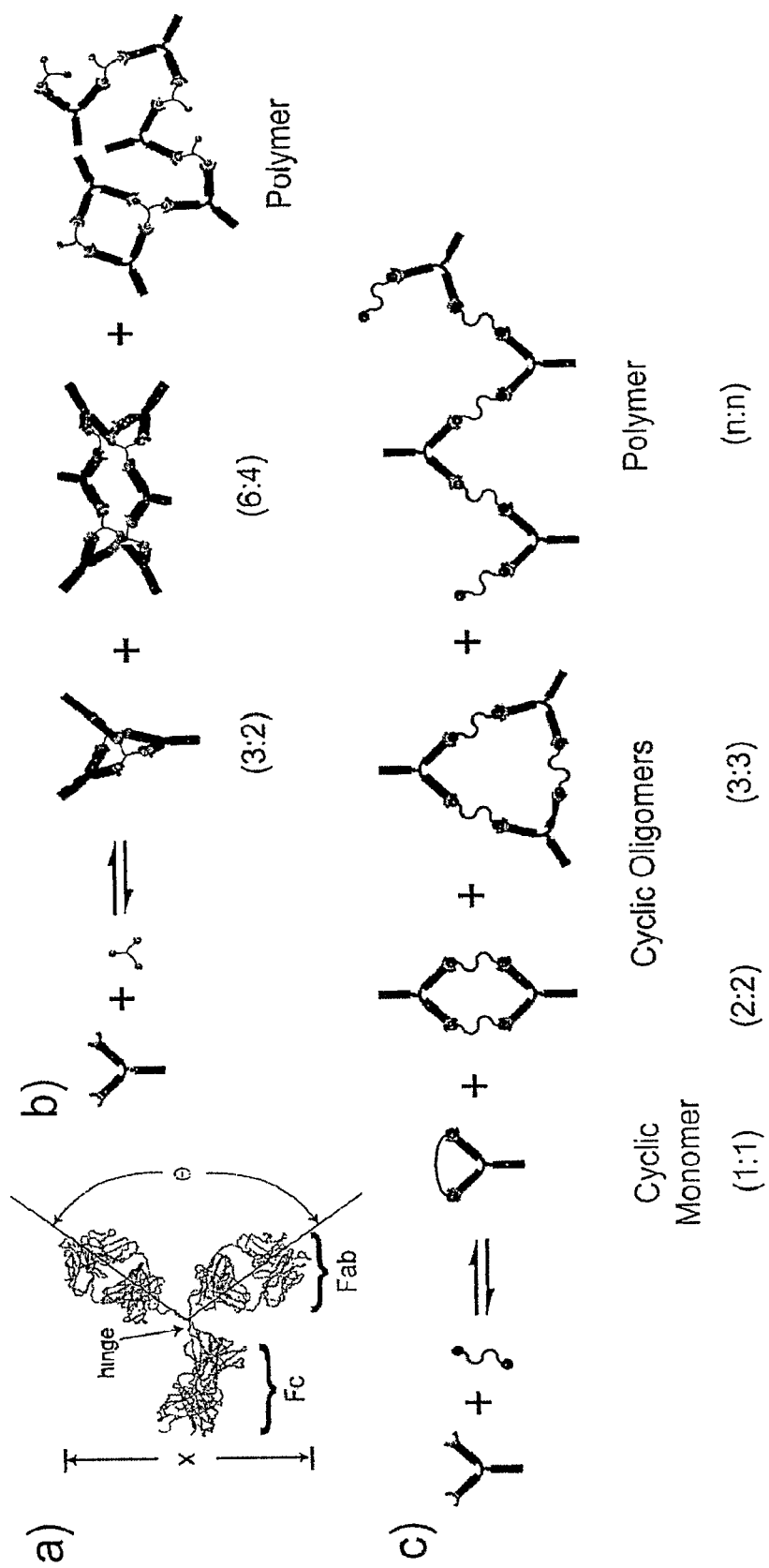
FIG. 2. (a) Crystal structure of an antibody with the dimensions labeled. The hinge region is flexible; this flexibility gives rise to a range of values for "Θ" and "x". The aggregates of antibodies (IgG) that can be formed by incubation with (b) trivalent hapten include: bicyclic antibody trimer, tricyclic antibody hexamer, and branched polymer; (c) divalent hapten include: cyclic dimer, cyclic trimer, and linear polymer.

Synthesis of Bi and Trivalent Ligands. The bivalent hapten (1) has the shortest (extended length~2.8 nm) ethylene glycol (EG2) linker between the two haptens (1); we chose this linker to promote water solubility and to prevent the binding of both haptens of the ligand to the same IgG (it is too short to allow this mode of binding to occur) (FIG. 2). We used O-(Benzotriazol-1-yl)-N,N,N',N'-tetramethyluronium hexafluorophosphate (HBTU) and N-hydroxybenzotriazole (HOBT) to couple 2,2'-(ethylenedioxy)diethylamine with 6-(2,4-dinitrophenylamino)hexanoic acid to Nα-Fmoc-Nε-DNP-L-Lysine to 2,2'-(Ethylenedioxy)bis-(ethylamine). Then a single step of Fmoc deprotection with 50% piperidine in DMF yielded 1.

We synthesized the bi and trivalent DNP compounds 4 and 5 with an initial coupling step to N-Fmoc-amido-dPEGn™-acid (purchased from Quanta Biodesign), followed by deprotection of Fmoc. The purified product was coupled to Tris-succinimidyl aminotriacetate (purchased from Pierce). By using different reactant ratios we achieved bi and trivalent DNP hapten products 4 and 5.

The synthesis of Nε-4-nitrophenyl-Lysine compound was synthesized by the procedure given in U.S. Pat. No. 6,630,004. We carried this compound through the set of reactions described above to yield the bi and trivalent 4-NP hapten products 2 and 3.

Figure 3:
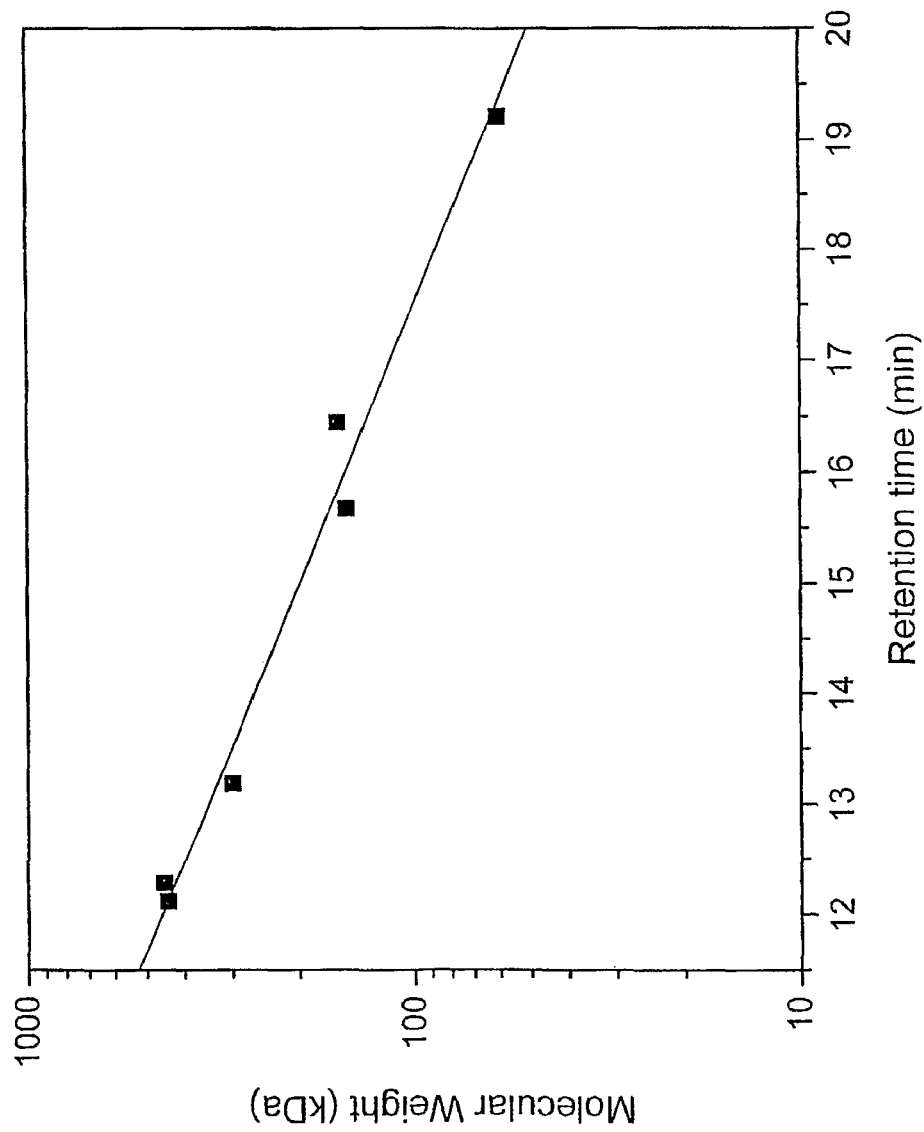
FIG. 3. Calibration plot for the size exclusion column relating the logarithm of molecular weights of proteins to their retention times. The proteins used as standards (in order of increasing retention time) were ferritin, IgG trimer ($IgG_3L_3$), IgG dimer ($IgG_2L_2$), IgG monomer (IgG), aldolase, and streptavidin. The x-axis (retention time) has been scaled for the dead-time (1.1 min) due to the presence of the guard column.
Figure 6:
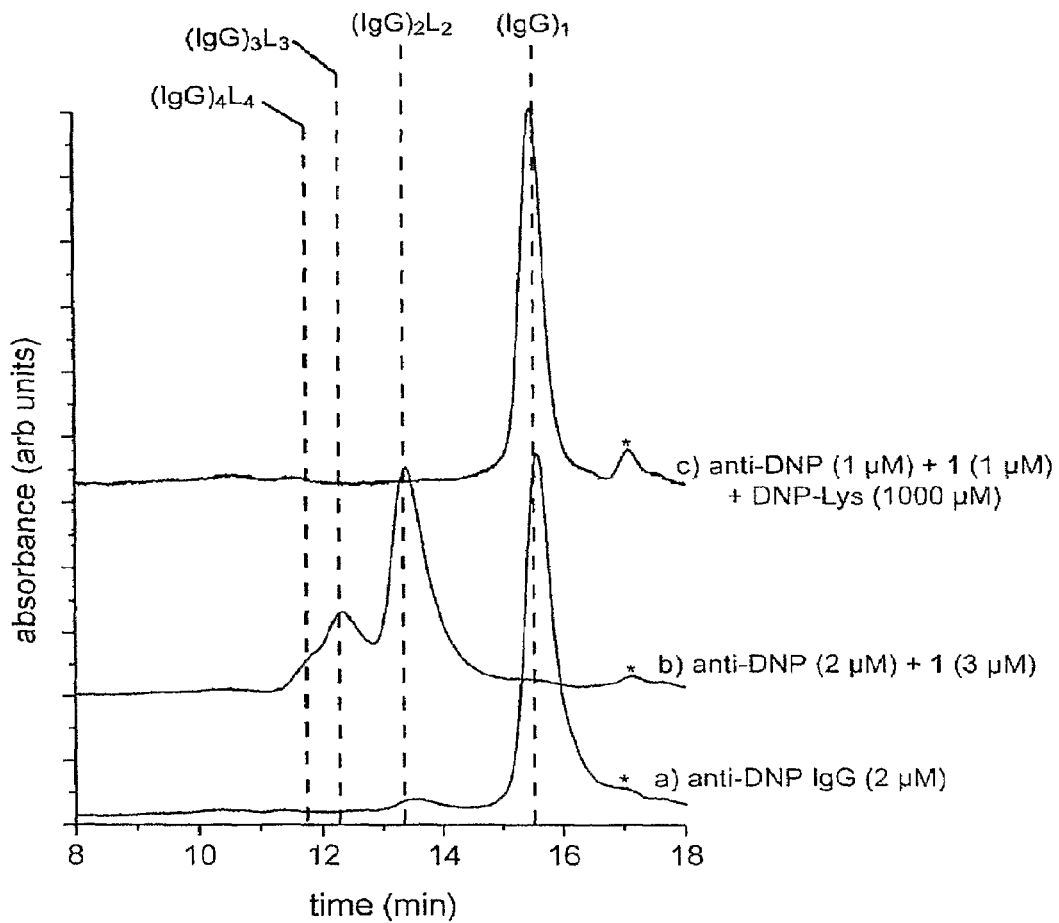
FIG. 6. Representative SE-HPLC chromatograms of (a) anti-2,4-DNP (2 µM), (b) anti-DNP (2 µM) after equilibration with 1.5 equiv. of 1 (3 µM), and (c) anti-DNP aggregates (1 µM, formed as in (b)) incubated with 1 mM of 6 for 90 sec before injection. The aggregates have completely dissociated into a single peak with the same retention time as that for monomeric IgG. The traces have been scaled to enable comparison between the different curves.

Validation of Size-Exclusion Chromatography (SE-HPLC) to Examine Aggregates of IgG. Size-exclusion chromatography (SE-HPLC) can resolve the cyclic aggregates of antibodies from each other and from monomeric IgG (FIG. 6). The commercially available purified IgG gave predominantly one peak by SE-HPLC (FIG. 6a) at a retention time (~15.6 min) consistent with the size of monomeric IgG (~150 kDa) based on a molecular weight calibration plot (FIG. 3). We formed aggregates in >90% conversion by incubating IgG (2 μM) with 5-10 equivalents of bi and trivalent molecules in chart 1 for 12 hours. Equilibrium titrations of this mAb anti-2,4-DNP (1.6 μM) with bivalent 2,4-DNP, 1, demonstrated that maximum conversion to cyclic aggregates occurred with the addition of 1-1.5 equivalents of 1 (1.6 μM). The chromatogram of this solution revealed two new peaks with retention times of 12.4 min ((IgG)$_3$L$_3$ (450 kD)) and 13.4 min ((IgG)$_2$L$_2$ (300 kD)) (FIG. 6b); the calibration plot allowed the assignment of the peaks (FIG. 3). The sharp peaks corresponding to the dimeric and trimeric aggregate demonstrate that the aggregates are kinetically stable on the timescale (30 min) of the HPLC run, and HPLC is an effective tool for following the amounts of these aggregates (and to determine the degree of conversion). These antibody aggregates dissociated rapidly (<1 min) in the presence of excess monovalent hapten (6) (1 μM anti-2,4-DNP; 1 μM 1; 1000 μM 6) (FIG. 6c).

Determination of dissociation constant of antibody and 2,4-DNP. The binding of DNP derivatives to anti-DNP quenches the fluorescence of tryptophan residues of the antibody. We conducted a fluorescence titration to determine the monovalent dissociation constant ($K_d^{affinity}$) of the IgG from clone (LO-DNP-2) for Ac2DNP-Lys, and obtained a value of 0.40±0.08 nM.

Development of ELISA Assay to Quantitate Active Anti-DNP IgG.

We developed an Enzyme-Linked Immunosorbent Assay (ELISA) to measure the amount of active IgG in different fractions of the purification procedure.

Figure 5:
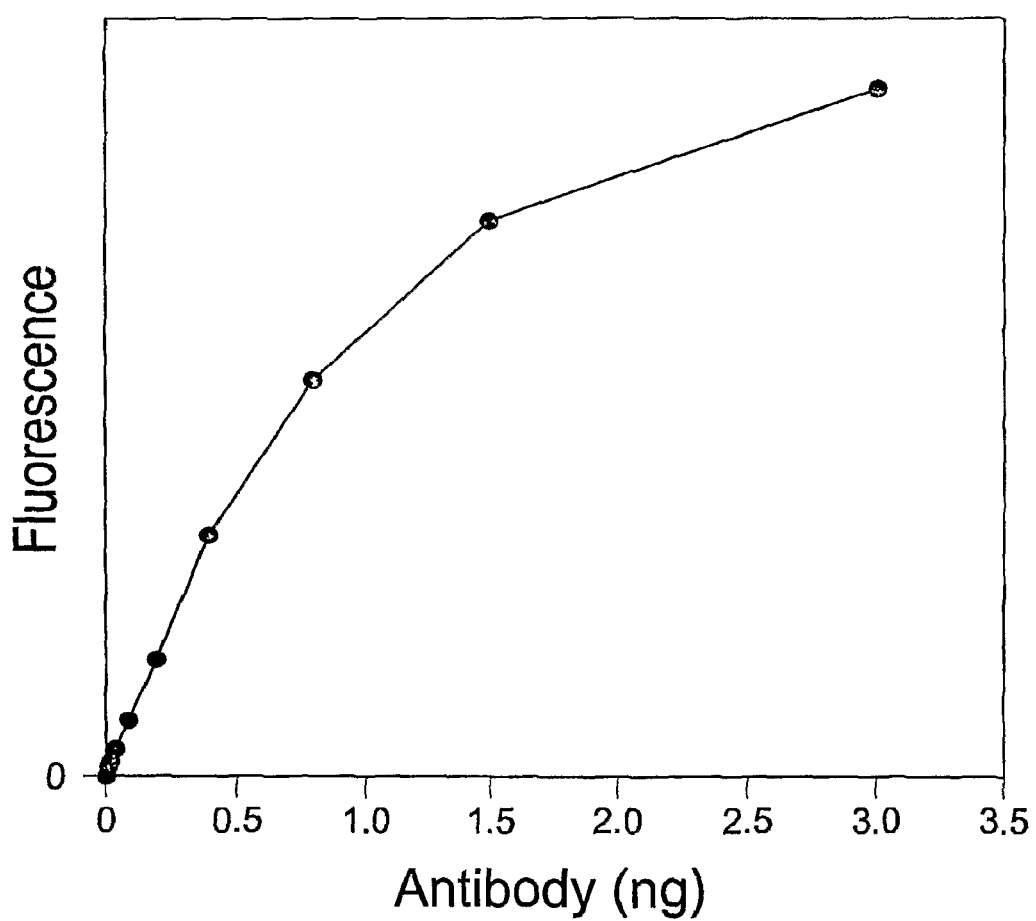
FIG. 5. ELISA standard curve (provided by the manufacturer) to allow detection of IgG. The wells of a microplate were adsorbed with hapten-conjugated BSA, washed, and then blocked with BSA. The indicated amounts of anti-hapten IgG was added to the wells. The wells were washed, incubated with a secondary IgG conjugated to Horse Radish Peroxidase, washed, and then treated with Amplex Red (Molecular Probes, Invitrogen). The reaction was allowed to proceed for 50 minutes and then examined using a spectrofluorimeter (excitation wavelength=530 nm, emission wavelength=590 nm).

We adsorbed a DNP-BSA conjugate to the surface of an ELISA plate. After treating the plate with the sample to be assayed and washing, we incubated the plate with a secondary antibody (anti-mouse from goat) conjugated to Horse Radish Peroxidase (HRP). We treated the plate with Amplex Red, and followed the HRP-catalyzed hydrolysis of this substrate fluorometrically. FIG. 5 shows the standard curve that allowed the quantitation of the amount of anti-DNP IgG bound to the surface.

Figure 7:
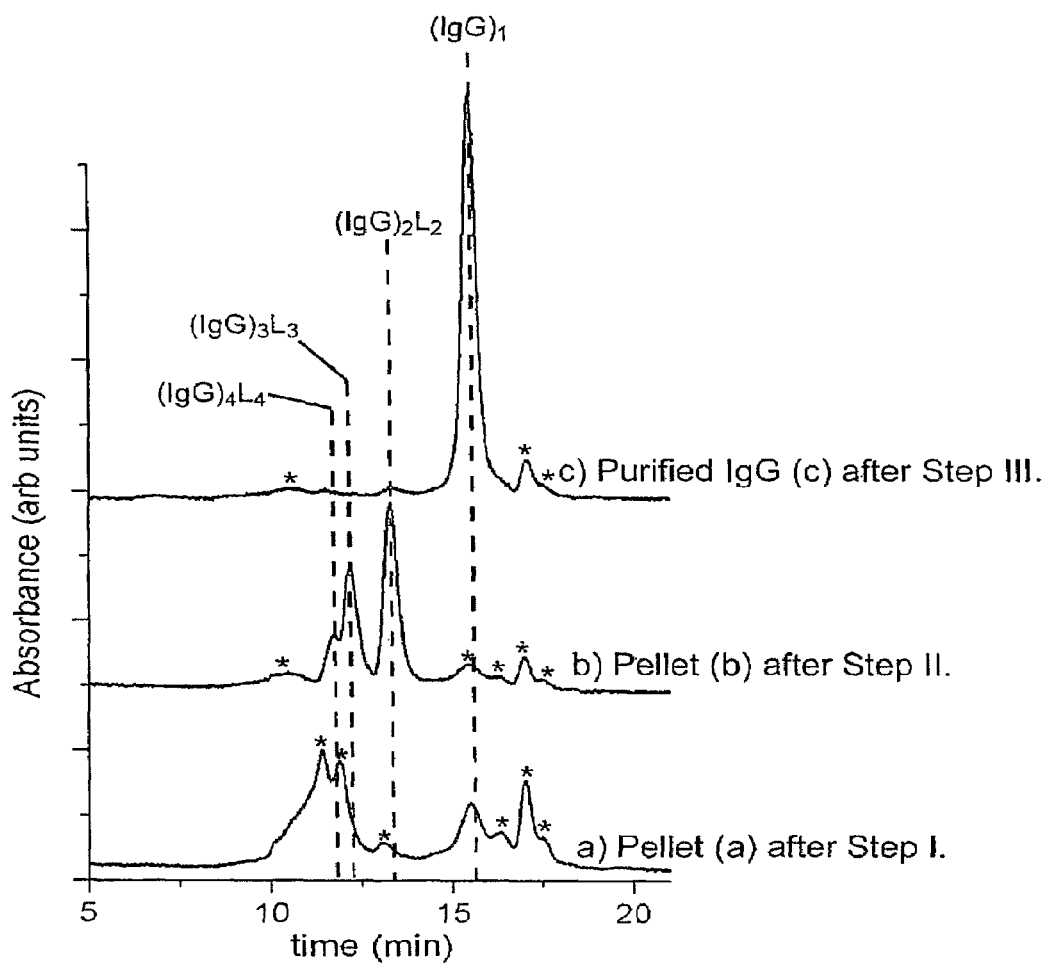
FIG. 7. Size exclusion chromatograms of anti-DNP ascites fluid. (a) Ascites fluid. (b) Ascites fluid after incubation with 1 (4 µM). We attribute the increased intensity at ~14 min to formation of cyclic dimers $(IgG)_2L_2$ (FIG. 2b). (c) The supernatant after treatment of (b) with 35% ammonium sulfate (see text and Step II, FIG. 4). The peaks corresponding to the serum proteins remain unchanged while the peak at ~14 min (assigned to $(IgG)_2L_2$) is reduced in intensity. Unidentified peaks (non-IgGs) are marked with asterisks (*). Injections were of a 1:10 dilution of ascites fluid.

Analysis of the Ascites Fluid by SE-HPLC. SE-HPLC analysis of the ascites fluid from rat containing LO-DNP-2 anti-2,4-DNP IgG showed that antibody (retention time 15.4 min) constituted a small fraction of the UV-active species (λ=214 nm) in ascites fluid (FIG. 7). Before beginning the purification, we assayed the ascites fluid for the presence of anti-2,4-DNP with two active Fab binding sites by titrating a 1:10 dilution of ascites fluid with 1 and analyzing the samples by SE-HPLC. The antibodies that form cyclic aggregates must have two active Fab sites (FIG. 2b). At 4 μM of 1, we observed an increase in peak intensity at the retention time (14 min) that corresponded to the antibody dimer (MW~300 kD) (FIG. 7b). The peak intensity at 14 minutes does not increase further with addition of 1 (up to 20 μM). These results indicate that we can induce the formation of IgG aggregates in complex biological fluids, even when the IgG antibodies are not the predominant species in the mixture.

Purification of Anti-2,4-DNP

Figure 8:
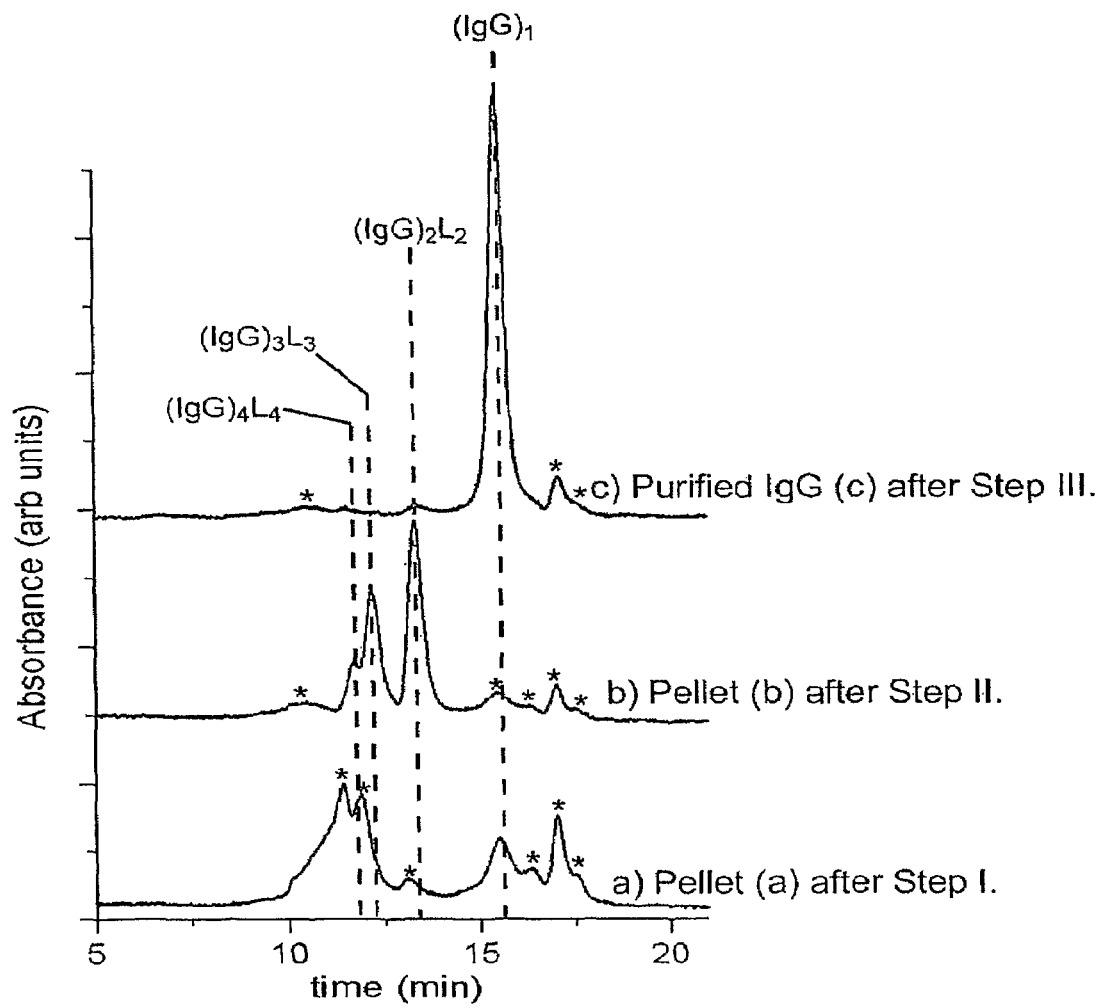
FIG. 8. Size exclusion chromatograms demonstrating the selective precipitation of cyclic aggregates of IgG with ammonium sulfate. (a) Serum proteins that precipitated with 35% ammonium sulfate (Step I, Pellet a, FIG. 4). (b) Cyclic aggregates (dimer, trimer, and tetramer) of IgG that precipitated after addition of 1 to the supernatant of the 35% ammonium sulfate fraction (the re-suspended pellet b from Step II, FIG. 4). (c) Monomeric IgG that resulted from dissociation of the cyclic aggregates (from (b)) by excess 7 (Step III, FIG. 4). The major peak has the same retention time as monomeric IgG. Injections were of 1 M of IgG (as estimated by the absorbance at λ=280 nm).

Step I. Removal of High Molecular Weight Impurities. The first step consisted of filtering the ascites fluid (0.5 mL) over glass wool to remove the majority of the liposaccharides. We rinsed the glass wool with an additional 0.5 mL of phosphate buffered saline (PBS: pH 7.4, 10 mM phosphate, 150 mM NaCl) for a final volume of 1 mL (diluting the ascites fluid two-fold). Addition of saturated ammonium sulfate solution (540 µL; to a final concentration of 1.4 M (35%)) to the diluted ascites fluid, followed by centrifugation, isolated the proteins having retention times (and thus molecular weights (300-600 kD)) similar to the antibody aggregates we were going to form as a pellet (FIG. 4a). The origin of selectivity for precipitation by ammonium sulfate of proteins by "salting-out" is not well-understood. Others have empirically determined that the selectivity is roughly dependent on molecular weight and pI: among similarly charged proteins, higher molecular weight proteins precipitate at lower concentrations of ammonium sulfate than do lower molecular weight proteins. SE-HPLC of the re-dissolved precipitate indicated that the pellet contained mostly high molecular weight (MW>400 kDa) impurities as well as a small amount of material with a retention time similar to monomeric IgG (FIG. 8a).

Step II. Isolation of Bivalently Active IgG$^{DNP}$ as Aggregates. The supernatant contained active IgG, inactive IgG, and serum proteins with molecular weights lower than that of IgG. The addition of 1 (to a final concentration of 4 µM) to the supernatant induced the aggregation of bivalently active IgG (FIG. 4b); these aggregates immediately formed a yellow precipitate (the color suggested the presence of 2,4-DNP). To ensure maximum recovery, we incubated the sample overnight at 4° C. Centrifugation (16,000 g, 30 min) of the sample isolated the pellet, which was re-dissolved in PBS for analysis by SE-HPLC. The three primary peaks in the SE-HPLC trace had the same retention times as the cyclic antibody aggregates: dimer, trimer, and tetramer (FIGS. 8b and 3). UV absorbance at 280 nm revealed the isolation of 0.8 mg of IgG in the pellet from 0.5 mL of ascites fluid. The distributions of the aggregates (between dimer, trimer, and tetramer) in this pellet differed from that obtained at equilibrium at low concentrations of antibody and low ionic strength (compare FIGS. 6b to 7b). The larger fraction of the higher-order aggregates (trimer and tetramer) in the AMS pellet (FIG. 4b) than in the lower ionic strength conditions could be due to one or more of the following possibilities: i) the distribution of aggregates depends on antibody concentration, ii) the high ionic strength (35% AMS) altered the equilibrium distribution of aggregates, and/or iii) the "salting-out" occurred faster than equilibration.

Step III. Dissociation of the Cyclic Aggregates with Monovalent DNP Yields Purified Anti-2,4-DNP. Addition of a large excess (~1 mM) of a 4-nitrophenylglucose (7, $K_d^{affinity}$=~0.5 µM) to the re-suspended pellet (FIG. 4b, estimated [IgG] from UV~7.4 µM) completely dissociated the IgG aggregates (FIGS. 4c and 8c). The SE-HPLC trace showed that the cyclic aggregates had cleanly dissociated to one species, which ran as a sharp peak with a retention time (15.5 min) corresponding to monomeric IgG (FIG. 8c). We used 7 to facilitate removal of the monovalent competitor by dialysis (see Step IV). We dialyzed (10 kDa MWCO membrane, 4° C.) the sample against 7 in order to prevent the re-formation of IgG aggregates When the sample that had been treated with 7 was dialyzed against PBS, a large fraction of the IgG antibodies re-formed higher-order aggregates.

Step IV. Removal of Monovalent Competitor. Exhaustive dialysis of the resultant material against PBS removed the low molecular weight bi- and monovalent haptens (as monitored by UV absorbance, λ=300-400 nm). The final product contained ~10% of the activity of the starting ascites fluid.

Analysis of the Proteins Remaining After Removal of the Bivalently Active IgG. SE-HPLC analysis of the supernatant that remained after removal of the antibody aggregates indicated that the majority of the material remaining in solution was a mixture of non-immunoglobulin serum proteins and IgGs that did not form aggregates (FIG. 7c). Addition of 1 (4 µM) to this supernatant did not result in further precipitation, indicating that all antibody capable of forming cyclic aggregates had been isolated with the first addition. We also tested the supernatant for active IgG DNP using the ELISA assay, and determined that there was no active anti-DNP detectable in the supernatant.

An increase in the concentration of ammonium sulfate in the supernatant to 1.8 M (45%) should precipitate any monomeric antibody remaining in the supernatant (45% AMS is the concentration routinely used to precipitate monomeric IgG from ascites fluid). After centrifugation, SE-HPLC analysis of the resulting pellet indicated that it contained protein(s) with the same retention time (and thus, molecular weight) as monomeric antibody (150 kD). The ELISA indicated that almost no starting activity was isolated in this pellet. This result reveals the lack of 2,4-DNP binding of this fraction, and indicates that IgG isolated in this pellet (if it is, indeed, an immunoglobulin) is improperly folded (or damaged) or is directed towards another (i.e., not 2,4-DNP) hapten.

Comparison of the Current Method to Other Purification Methods

From the integration of the SE-HPLC chromatograms (FIG. 7), assuming that the molar absorptivity at 214 nm of the different species was the same, the molecular purity of the material purified using this method was ~90%. The IgG peak required two Gaussian curves (centered at 15.5 min and 16.0 min) to completely fit the shoulder. Both of these peaks contain bivalently active IgG because upon incubation with 1, both peaks disappear and are replaced by two peaks with retention times expected for IgG dimer.

Figure 9:
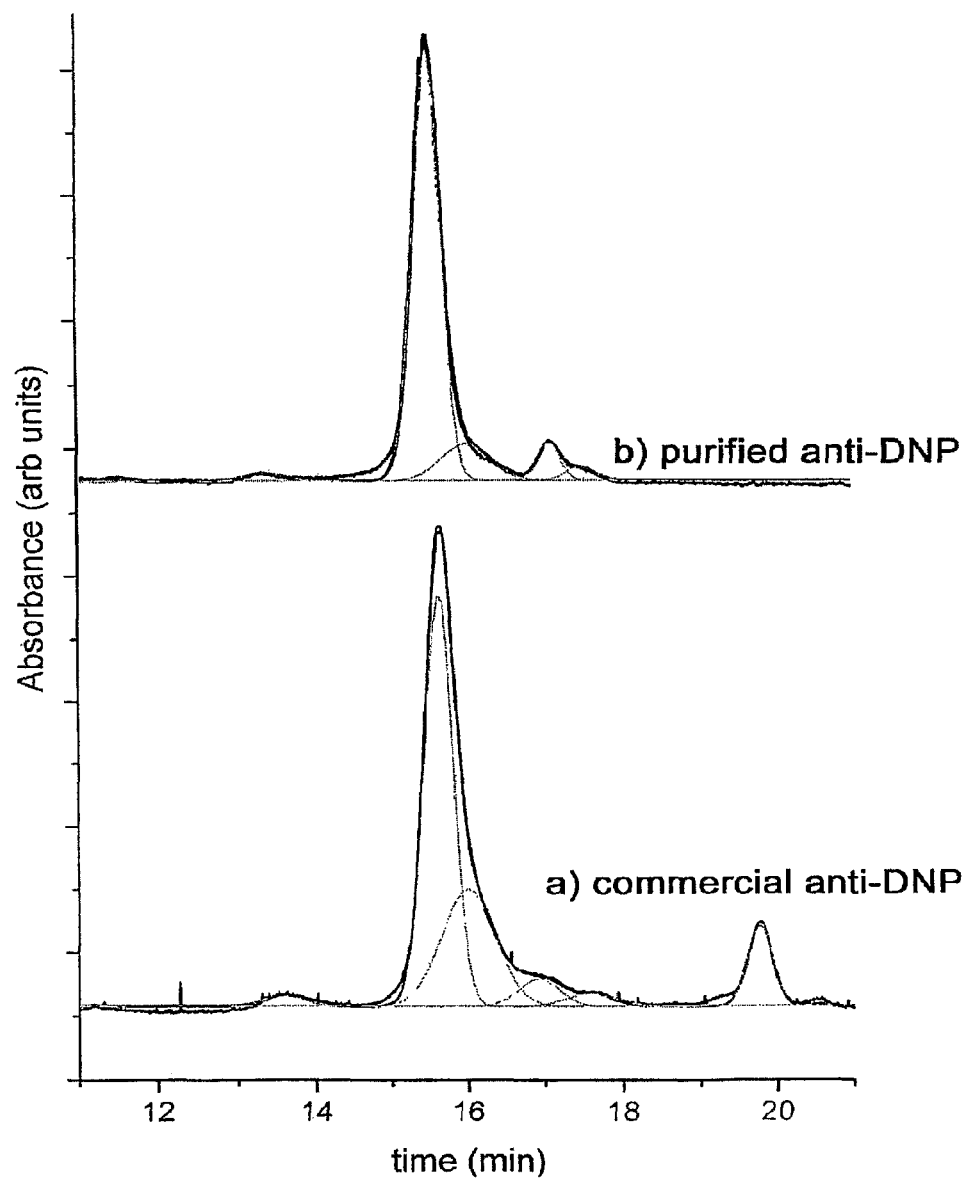
FIG. 9. Gaussian curves fit to size-exclusion chromatograms of (a) anti-DNP IgG (clone: LO-DNP-2) as received from a commercial source (1.6 µM), and (b) anti-DNP IgG (clone: LO-DNP-2) purified using the method described in this paper (1 µM). Black: Raw data; Gray: individual Gaussian curves used to fit the data; Black: the sum of the Gaussians (superimposed with Raw data).

We also analyzed commercially available purified anti-2, 4-DNP (from the same clone as the ascites fluid) by SE-HPLC (FIG. 9). The chromatogram revealed the presence of impurities with molecular weights both higher and lower than that of IgG. The molecular purity of the commercial antibody (as determined by integrating the chromatogram) is 80%. The second Gaussian curve (centered at 16.0 min) is a larger percent of the total area of the commercial anti-2,4-DNP (32%) than the material purified using ammonium sulfate precipitation (13%).

Discussion

Generalization to Other Antibodies and the Influence of $K_d$.

The thermodynamic stability of the aggregates is a key factor in the effectiveness of this purification technique. Theoretical studies predict that this stability is directly related to the monovalent affinity of the antibody for the hapten and the concentration of antibody.

Preliminary investigations of the applicability of this purification technique to monoclonal antibodies with lower affinities for their haptens than anti-DNP have supported this theoretical prediction. We have successfully precipitated aggregates of IgG DNP using bi and trivalent DNP ($K_d^{affinity}$~8 nM) haptens, and bi and trivalent 4-NP ($K_d^{affinity}$~0.5 µM). Similar attempts with a mAb anti-fluorescein IgG ($K_d^{affinity}$~10 nM) using a bivalent fluorescein derivative also resulted with success.

Extension of the Purification Technique to Other Antibody Isotypes.

The majority of previous studies of cyclic aggregates use bivalent (IgG or IgE) antibodies. Incubation of an anti-lactose IgM (a pentameric antibody which is decavalent) with bivalent lactose haptens resulted in binding of both haptens of the ligand to the same IgM and not in IgM aggregates (as determined by sedimentation). Nevertheless, with optimization of bivalent hapten length, this procedure is envisioned as being further applied to the purification of IgMs.

Conclusions

Ammonium sulfate precipitation of cyclic aggregates of antibodies can separate bivalently active antibody from inactive antibody, as well as from other serum proteins in ascites fluid.

This method is, to date, the only purification procedure for monoclonal antibodies that selectively isolates monoclonal IgGs with two active Fab binding sites starting from a crude biological source of antibodies.

What are the Advantages of the Method?

The isolated material is guaranteed to have two fully active Fab binding sites because both sites are required to form the aggregates.

It does not require chromatographic purification.

What are the Limitations of the Method?

The primary limitation of this technique is the synthetic accessibility of bi and trivalent haptens. Our model antibody is directed against a small molecule hapten. The requirement for a synthetically accessible bivalent derivative of the hapten may limit the application of this technique to purify antibodies directed towards a recognition site created by the tertiary structure of a large or membrane-bound protein.

For some antibodies directed against proteins, the bivalent hapten could be a dimer of the protein antigen.

Furthermore, mimotopes of such protein constructs are usually short peptide sequences that can be designed to be synthesized as a bi or trivalent molecule. The mimotopes usually are searched for through binding assays towards peptide libraries or phage display.

What are the Applications?

We have already used antibodies purified by this method to perform physical-organic experiments to characterize the thermodynamics of the formation of the hapten driven aggregates. These purified antibodies are also necessary for a number of kinds of biophysical research in which homogeneous antibodies with two active Fab regions are required.

This technique is useful in many applications that require purifying substantial quantities of antibodies for common biological and clinical analyses, and additionally for human therapeutics.

This technique is also useful for fractionating mixtures of polyclonal antibodies from serum based on their affinity for a given hapten and/or their specificity.

For some antibodies directed against proteins, the bivalent hapten might be a dimer of the protein antigen (or a functional bivalent peptide).

Definitions

Unless defined otherwise, technical and scientific terms used herein have the same meaning as commonly understood by one of ordinary skill in the art to which this invention belongs. See, e.g., Dorland's illustrated medical dictionary (30$^{th}$ Edition), D. M. Anderson, P. D. Novak, J. Keith and M. A. Elliott, Eds. Saunders (an Imprint of Elsevier), Philadelphia, Pa., 2003.

The term "hapten" refers to a small molecule, not antigenic by itself, that can react with antibodies of appropriate specificity and elicit the formation of such antibodies when conjugated to a larger antigenic molecule, usually a protein, called the carrier.

The term "affinity" refers to the strength of interaction between a single antigen-binding site and a single antigenic determinant (and thus the stereochemical compatibility between them), most accurately applied to interactions among simple, uniform antigenic determinants such as haptens.

The term "avidity" refers to the strength of binding between antibody and a complex antigen. Since the antigen has more than one determinant and the determinants may vary from one another, avidity expresses the overall interaction between antigen and antibody; it is, however, greater than the sum of the affinities for the single determinants, since the effective multivalency of the antigen gives rise to a cooperative "bonus" effect. Avidity is often represented by $K_a$ (the value of the association constant for the reaction $Ab+Ag \leftrightarrows AbAg$). Avidity is a function of the techniques used in its measurement and can be expressed only in arbitrary units.

The term "antigen" refers to any substance capable, under appropriate conditions, of inducing a specific immune response and of reacting with the products of that response, that is, with specific antibody or specifically sensitized T lymphocytes, or both. Antigens may be soluble substances, such as toxins and foreign proteins, or particulate, such as bacteria and tissue cells, however, only the portion of the protein or polysaccharide molecule known as the antigenic determinant combines with the antibody or a specific receptor on a lymphocyte.

The term "antibody" refers to an immunoglobulin molecule that has a specific amino acid sequence by virtue of which it interacts only with the antigen that induced its synthesis in cells of the lymphoid series (especially plasma cells), or with antigen closely related to it. Antibodies are classified in groups named according to their modes of action, such as agglutinins, bacteriolysins, heomolysins, opsonins, precipitins, and others. The term antibody is used in the broadest sense and specifically covers intact monoclonal antibodies, polyclonal antibodies, and antibody fragments so long as they exhibit the desired biological activity.

The term "Fab" refers to either of two identical fragments, each containing an antigen combining site, obtained by papain cleavage of the IgG, now generally used as an adjective, also called "Fab'" fragment (e.g., Fab region, segment, to refer to an "arm" of any immunoglobulin monomer, i.e., one light chain and the adjoining heavy chain $V_H$ and $C_H 1$ domains).

The term "F(ab)$_2$" refers to the fragment containing both Fab regions and the hinge region connecting them by interchain disulfide bonds obtained by pepsin cleavage of the IgG molecule, also called "F(ab')$_2$" fragment.

The term "Fv" means the fragment of the antibody containing the variable domain(s).

"Antibody fragments" comprise a portion of an intact antibody, generally the antigen binding or variable region of the intact antibody. Examples of antibody fragments include Fab, Fab', F(ab')$_2$, and Fv fragments; diabodies; linear antibodies; single-chain antibody molecules; and bivalent and bispecific antibodies.

The term "bivalent" refers to an antibody or antibody fragment thereof in which each of two antigen-binding sites are specific for the same or separate antigenic determinant, or a hapten in which each of two antibody reactive sites are specific for the same or separate antibody paratope.

The term "multivalent hapten" refers to a hapten in which each of multiple antibody reactive sites (e.g., 2 (bivalent), 3 (trivalent), 4 (tetravalent), 5 (pentavalent), 6 (hexavalent), etc) are specific for the same or separate antibody paratope.

The term "bispecific" refers to an antibody or antibody fragment thereof in which each of two antigen-binding sites are specific for separate antigenic determinants, or a hapten in which each of two antibody reactive sites are specific for the same or separate antibody paratopes.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein 1975 Nature 256:495, they may be made and isolated from ascites fluid, or they may be made by recombinant DNA methods (see, e.g., U.S. Pat. No. 4,816,567, Cabilly et al.). The "monoclonal antibodies" may also be isolated from phage antibody libraries using the techniques described in Clackson et al. 1991 Nature 352:624-628 and Marks et al. 1991 J Mol Biol 222: 581-597, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., supra; Morrison et al. 1984 Proc Natl Acad Sci USA 81:6851-6855).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework residues of the human immunoglobulin are replaced by corresponding non-human residues. Furthermore, humanized antibodies may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details see: Jones et al. 1986 Nature 321:522-525; Reichmann et al. 1988 Nature: 332:323-329; and Presta 1992 Curr Op Struct Biol 2:593-596. The humanized antibody includes a primate antibody wherein the antigen-binding region of the antibody is derived from an antibody produced by immunizing macaque monkeys with the antigen of interest.

As used herein, the term "purified" refers to a molecule (e.g., an antibody) having been separated from a component of the composition in which it was originally present. Thus, for example, an antibody has been purified to a level not found in nature. A "substantially pure" molecule is a molecule that is lacking in most other components (e.g., 30, 40, 50, 60, 70, 75, 80, 81, 82, 83, 84, 85, 86, 87, 88, 89, 90, 91, 92, 93, 94, 95, 96, 97, 98, 99, 100% free of contaminants). By opposition, the term "crude" means molecules that have not been separated from the components of the original composition in which it was present (e.g., ascites fluid comprising monoclonal antibody). Therefore, the terms "separating" or "purifying" refers to methods by which one or more components of the sample are removed from one or more other components of the sample. Antibody sources may include plasma, serum, ascites, milk, and cell culture supernatant, as well as commercially available antibody preparations. The source of the antibody may include all or parts of the components originally found in a natural source. Thus, apart from antibody, the antibody source may include other components, such as proteins, carbohydrates, lipids or nucleic acids. In one embodiment, a separating or purifying step removes at least about 50% (e.g., 50, 55, 60, 65, 70, 75, 80, 85, 90, 95, 96, 97, 98, 99, and 100%) of the other components present in the sample from the desired component. In another embodiment, the purifying step removes at least about 80% (e.g., 80, 81, 82, 83, 84, 85, 86, 87, 88, 89, 90, 91, 92, 93, 94, 95, 96, 97, 98, 99, and 100%) and, in a further embodiment, at least about 95% (e.g., 95, 96, 97, 98, 99, and 100%) of the other components present in the sample from the desired component.

Immunoglobulins

The methods of the invention are applicable to immunoglobulins of different isotype classes. Each immunoglobulin class has a characteristic type of heavy chain. Thus IgG possesses γ chains; IgM, μ chains; IgA, α chains; IgD, δ chains; and IgE, ε chains. Variation in heavy chain structure within a class gives rise to immunoglobulin subclasses. For example, the human IgG pool consists of four subclasses reflecting four distinct types of heavy chain. The properties of the immunoglobulins vary between the different classes. In secretions, IgA occurs in a dimeric form (sIgA) in association with a protein chain termed the secretory component. The serum concentration of sIgA is very low, whereas the level in intestinal secretions can be very high. Table A provides the physicochemical properties of human immunoglobulin classes.

TABLE A

Physicochemical properties of human immunoglobulin classes

| | IgG1 | IgG2 | IgG3 | IgG4 | IgM | IgA1 | IgA2 | sIgA | IgD | IgE |
|---|---|---|---|---|---|---|---|---|---|---|
| Heavy chain | γ1 | γ2 | γ3 | γ4 | μ | $α_1$ | $α_2$ | $α_1$ or $α_2$ | δ | ε |
| Mean serum concentration (mg/ml) | 9 | 3 | 1 | 0.5 | 1.5 | 3.0 | 0.5 | 0.05 | 0.03 | 0.00005 |

TABLE A-continued

| Physicochemical properties of human immunoglobulin classes | | | | | | | | | | |
|---|---|---|---|---|---|---|---|---|---|---|
| | IgG1 | IgG2 | IgG3 | IgG4 | IgM | IgA1 | IgA2 | sIgA | IgD | IgE |
| Sedimentation constant | 7S | 7S | 7S | 7S | 19S | 7S | 7S | 11S | 7S | 8S |
| Molecular weight (KDa) | 146 | 146 | 170 | 146 | 970 | 160 | 160 | 385 | 184 | 188 |
| Half-life (days) | 21 | 20 | 7 | 21 | 10 | 6 | 6 | ? | 3 | 2 |
| % intravascular distribution | 45 | 45 | 45 | 45 | 80 | 42 | 42 | trace | 75 | 50 |
| Carbohydrate (%) | 2-3 | 2-3 | 2-3 | 2-3 | 12 | 7-11 | 7-11 | 7-11 | 9-14 | 12 |

Figure 10:
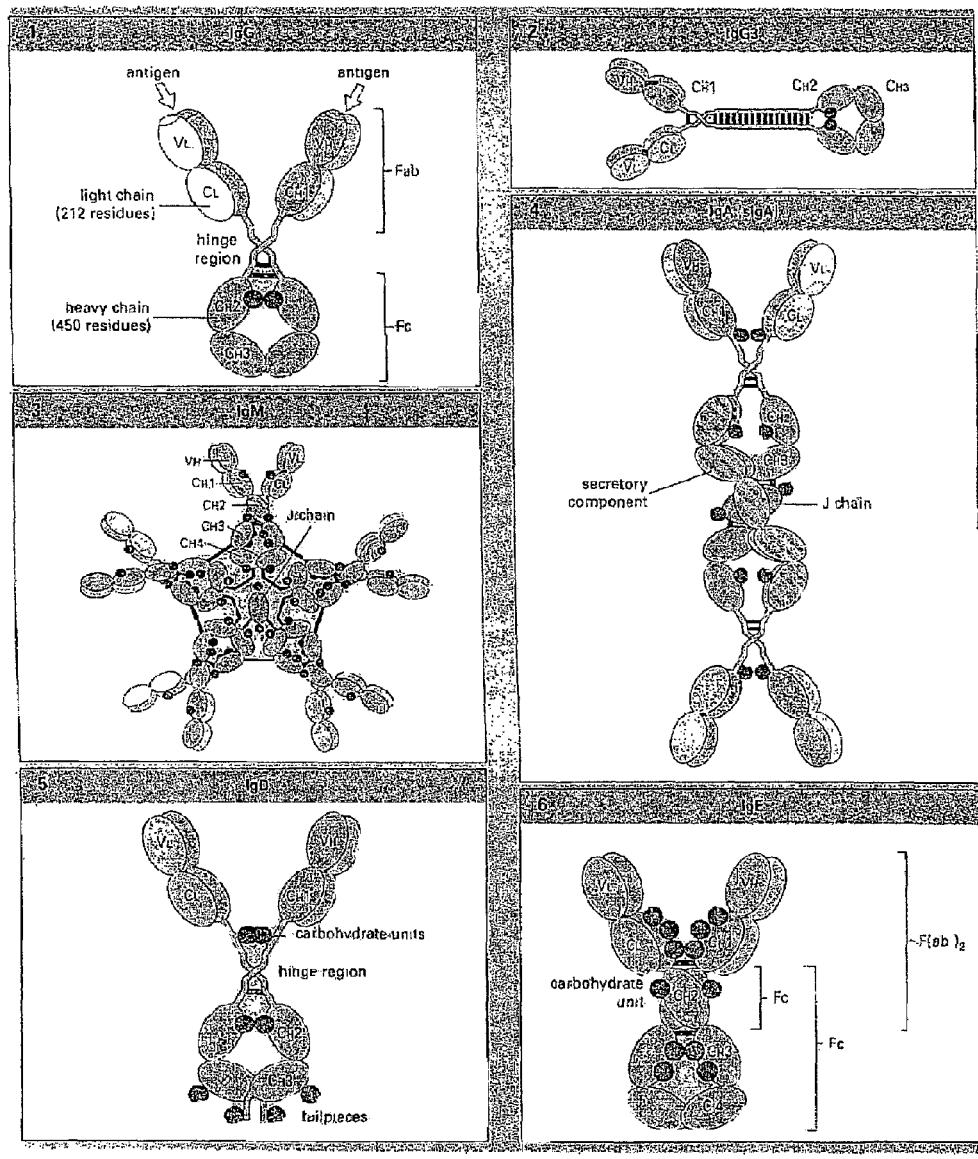
FIG. 10. Structural characteristics of various immunoglobulins.

The structural characteristics of various human immunoglobulins are shown in FIG. 10. Carbohydrate side chains are shown in blue. Inter heavy (H) chain disulfide bonds are shown in red, but interchain bonds between H and L chains are omitted. A model of IgG1 indicating the globular domains of H and L chains is shown in panel 1. Note the apposition of the $C_H3$ domains and the separation of the CH2 domains. The carbohydrate units lie between the $C_H2$ domains. The polypeptide chain structure of human IgG3 is shown in panel 2. IgM H chains have five domains with disulfide bonds cross-linking adjacent $C_H3$ and $C_H4$ domains are shown in panel 3. The possible location of the J chain is also shown. IgM does not have extended hinge regions, but flexion can occur about the $C_H2$ domains. The secretory component of sIgA is probably wound around the dimer and attached by two disulfide bonds to the $C_H2$ domain of one IgA monomer, as shown in panel 4. The J chain is required to join the two subunits. Panel 5 is diagram of IgD showing the domain structure and a characteristically large number of oligosaccharide units. Note also the presence of a hinge region and short octapeptide tailpieces. IgE can be cleaved by enzymes to give the fragments $F(ab')_2$, Fc, and Fc', as shown in panel 6.

Antibody Preparation

The antibodies purified by the methods of the invention can be from any source. For example, non-limiting examples of sources of antibodies include plasma, serum, ascites, milk, cell culture supernatant, and commercially available antibody preparations. The antibodies may be polyclonal antibodies, monoclonal antibodies, humanized and human antibodies, and antibody fragments.

(a) Polyclonal Antibodies

Polyclonal antibodies are generally raised in animals by multiple subcutaneous or intraperitoneal injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining 1 mg or 1 μg of the peptide or conjugate (for rabbits or mice, respectively) with 3 volumes of Freund's complete adjuvant and injecting the solution intradermally at multiple sites. One month later the animals are boosted with 1/5 to 1/10 the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(b) Monoclonal Antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler and Milstein 1975 Nature 256:495, they may be derived from ascites fluid, or they may be made by recombinant DNA methods (Cabilly et al., supra).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding in Monoclonal Antibodies: Principles and Practice, pp. 59-103, Academic Press, 1986).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-1 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies (Kozbor 1984 *J Immunol* 133:3001; Brodeur et al. in *Monoclonal Antibody Production Techniques and Applications*, pp. 51-63, Marcel Dekker, Inc., New York, 1987).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson and Pollard 1980 *Anal Biochem* 107:220.

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose™, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al. 1993 *Curr Opinion in Immunol* 5:256-262 and Plückthun 1992 *Immunol Rev* 130: 151-188.

In a further embodiment, antibodies or antibody fragments can be isolated from antibody phage libraries generated using the techniques described in McCafferty et al. 1990 *Nature* 348:552-554, using the proper antigen to select for a suitable antibody or antibody fragment. Clackson et al. 1991 *Nature* 352:624-628 and Marks et al. 1991 *J Mol Biol* 222:581-597 describe the isolation of murine and human antibodies, respectively, using phage libraries. Subsequent publications describe the production of high affinity (nM range) human antibodies by chain shuffling (Mark et al. 1992 *Bio/Technology* 10:779-783, as well as combinatorial infection and in vivo recombination as a strategy for constructing very large phage libraries (Waterhouse et al. 1993 *Nuc Acids Res* 21:2265-2266). Thus, these techniques are viable alternatives to traditional monoclonal antibody hybridoma techniques for isolation of "monoclonal" antibodies.

The DNA also may be modified, for example, by substituting the coding sequence for human heavy- and light-chain constant domains in place of the homologous murine sequences (Cabilly et al., supra; Morrison, et al. 1984 *Proc Nat Acad Sci USA* 81:6851), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

For diagnostic applications, the variants herein derived from antibodies typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$; a fluorescent or chemiluminescent compound, such as fluorescein isothiocyanate, rhodamine, or luciferin; radioactive isotopic labels, such as, e.g., $^{125}I$, $^{32}P$, $^{14}C$, or $^3H$; or an enzyme, such as alkaline phosphatase, beta-galactosidase, or horseradish peroxidase.

Any method known in the art for separately conjugating the polypeptide variant to the detectable moiety may be employed, including those methods described by Hunter et al. 1962 *Nature* 144:945; David et al. 1974 *Biochemistry* 13:1014; Pain et al. 1981 *J Immunol Meth* 40:219; and Nygren, J. 1982 *Histochem and Cytochem* 30:407.

(c) Humanized and Human Antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. 1986 *Nature* 321:522-525; Riechmann et al. 1988 *Nature* 332:323-327; Verhoeyen et al. 1988 *Science* 239:1534-1536), by substituting rodent CDRs or CDR sequences for the corresponding sequences of a human antibody. Accordingly, such "humanized" antibodies are chimeric antibodies (Cabilly et al., supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity: According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al. 1993 *J Immunol* 151:2296; Chothia and Lesk 1987 *J Mol Biol* 196:901). Another method uses a particular framework derived from the consensus sequence of all human antibodies of a particular subgroup of light or heavy chains. The same framework may be used for several different humanized antibodies (Carter et al. 1992 *Proc Natl Acad Sci USA* 89:4285; Presta et al. 1993 *J Immunol* 151:2623).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al. 1993 *Proc Natl Acad Sci USA* 90:2551-255; Jakobovits et al. 1993 *Nature* 362:255-258; Bruggermann et al. 1993 *Year in Immuno* 7:33. Human antibodies can also be produced in phage-display libraries (Hoogenboom and Winter 1991 *J Mol Biol* 227:381; Marks et al. 1991 *J Mol Biol* 222:581).

(d) Antibody Fragments

Various techniques have been developed for the production of antibody fragments. Traditionally, these fragments were derived via proteolytic digestion of intact antibodies (see, e.g., Morimoto et al., 1992 *Journal of Biochemical and Biophysical Methods* 24:107-117 and Brennan et al. 1985 *Science* 229:81). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al. 1992 *Bio/Technology* 10:163-167). Alternatively, F(ab')$_2$ fragments can be isolated directly from recombinant host cell culture. Other techniques for the production of antibody fragments will be apparent to the skilled practitioner.

Uses for the Purified Antibody

Many uses for antibodies which have been purified using the disclosed methods are contemplated, including diagnostic and therapeutic uses. Various diagnostic and therapeutic uses for antibodies have been reviewed in Goldenberg et al. 1990 Semin Cancer Biol 1:217-225, Beck et al. 1990 Semin Cancer Biol 1:181-188, Niman, 1990 Immunol Ser 53:189-204 and Endo 1990 *Nippon Igaku Hoshasen Gakkai Zasshi* (Japan) 50:901-909, for example.

Antibodies can also be used for in vitro or in vivo immunodiagnosis of various diseases such as cancer. To facilitate this diagnostic use, an antibody which binds a tumor associated antigen can be conjugated with a detectable marker (e.g., a chelator which binds a radionuclide). For example, an antibody having specificity for the tumor associated antigen CEA can be used for imaging of colorectal and thyroid carcinomas. The anti-p185$^{HER2}$ antibody can be used for detecting cancers characterized by amplification of the HER2 proto-oncogene. Other non-therapeutic, diagnostic uses for the antibody will be apparent to the skilled practitioner.

For diagnostic applications, the antibody typically will be labeled directly or indirectly with a detectable moiety. The detectable moiety can be any one which is capable of producing, either directly or indirectly, a detectable signal. For example, the detectable moiety may be a radioisotope, such as $^3$H, $^{14}$C, $^{32}$P, $^{35}$S, or $^{125}$I; a fluorescent or chemiluminescent compound, such as fluorescein isothiocyanate, rhodamine, or luciferin; or an enzyme, such as alkaline phosphatase, beta-galactosidase or HRP.

Any method known in the art for separately conjugating the antibody to the detectable moiety may be employed, including those methods described by Hunter et al. 1962 *Nature* 144:945; David et al. 1974 *Biochemistry* 13:1014; Pain et al. 1981 *J Immunol Meth* 40:219; and Nygren 1982 *J Histochem and Cytochem* 30:407.

The antibodies described herein can be used in immunoassays, such as enzyme immunoassays.

The antibodies of the present invention may be employed in any known assay method, such as competitive binding assays, direct and indirect sandwich assays, and immunoprecipitation assays (Zola in *Monoclonal Antibodies: A Manual of Techniques*, pp. 147-158, CRC Press, Inc., 1987.

Competitive binding assays rely on the ability of a labeled standard to compete with the test sample analyte for binding with a limited amount of antibody. The amount of analyte in the test sample is inversely proportional to the amount of standard that becomes bound to the antibody. To facilitate determining the amount of standard that becomes bound, the antibody generally is insolubilized before or after the competition, so that the standard and analyte that are bound to the antibody may conveniently be separated from the standard and analyte which remain unbound.

The antibodies also are useful for the affinity purification of an antigen of interest from recombinant cell culture or natural sources.

Therapeutic uses for the antibodies purified using the method described herein are also contemplated. For example, the antibody can be used for redirected cytotoxicity (e.g., to kill tumor cells), as a vaccine adjuvant, for delivering thrombolytic agents to clots, for delivering immunotoxins to tumor cells, for converting enzyme activated prodrugs at a target site (e.g., a tumor), for treating infectious diseases or targeting immune complexes to cell surface receptors. Therapeutic formulations of the antibody are prepared for storage by mixing the antibody having the desired degree of purity with optional physiologically acceptable carriers, excipients, or stabilizers (Remington's Pharmaceutical Sciences, 16th edition, Osol, A., Ed., 1980), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The antibody also may be entrapped in microcapsules prepared, for example, by coacervation techniques or by interfacial polymerization (for example, hydroxymethylcellulose or gelatin-microcapsules and poly-[methylmethacylate] microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, supra.

The antibody to be used for in vivo administration must be sterile. This is readily accomplished by filtration through sterile filtration membranes, prior to or following lyophilization and reconstitution. The antibody ordinarily will be stored in lyophilized form or in solution.

Therapeutic antibody compositions generally are placed into a container having a sterile access port, for example, an intravenous solution bag or vial having a stopper pierceable by a hypodermic injection needle.

The route of antibody administration is in accord with known methods, e.g., injection or infusion by intravenous, intraperitoneal, intracerebral, intramuscular, intraocular, intraarterial, or intralesional routes, or by sustained release systems as noted below. The antibody is administered continuously by infusion or by bolus injection.

Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al. 1981 *J Biomed Mater Res* 15:167-277 and Langer 1982 *Chem Tech* 12:98-105 or poly(vinylalcohol)], polylactides (U.S. Pat. No. 3,773,919, EP 58,481), copolymers of L-glutamic acid and gamma ethyl-L-glutamate (Sidman et al. 1983 *Biopolymers* 22:547-556), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(-)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for antibody stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release antibody compositions also include liposomally entrapped antibody. Liposomes containing the antibody are prepared by methods known per se: DE 3,218, 121; Epstein et al. 1985 *Proc Natl Acad Sci USA* 82:3688-3692; Hwang et al. 1980 *Proc Natl Acad Sci USA* 77:4030-4034; EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200-800 Angstroms) unilamellar type in which the lipid content is greater than about 30 mol. % cholesterol, the selected proportion being adjusted for the optimal antibody therapy.

An effective amount of antibody to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 µg/kg to up to 10 mg/kg or more, depending on the factors mentioned above. Typically, the clinician will administer antibody until a dosage is reached that achieves the desired effect. The progress of this therapy is easily monitored by conventional assays.

Protein Precipitation using Ammonium Sulfate

One aspect of the invention relates to the use of salts (e.g., ammonium sulfate) to precipitate protein. The solubility of globular proteins increases upon the addition of salt (<0.15 M), an effect termed salting-in. At higher salt concentrations, protein solubility usually decreases, leading to precipitation; this effect is termed salting-out (Green A. A. and Hughes W. L., 1955 *Methods Enzymol* 1:67-90). Salts that reduce the solubility of proteins also tend to enhance the stability of the native conformation. In contrast, salting-in ions are usually denaturants.

The mechanism of salting-out is based on preferential solvation due to exclusion of the cosolvent (salt) from the layer of water closely associated with the surface of the protein (hydration layer). The hydration layer, typically 0.3 to 0.4 g water per gram protein (Rupley J. A. et al. 1983 *Trend Biochem Sci* 8:18-22), plays a critical role in maintaining solubility and the correctly folded native conformation. There are three main protein-water interactions: ion hydration between charged side chains (e.g., Asp, Glu, Lys), hydrogen bonding between polar groups and water (e.g., Ser, Thr, Tyr, and the main chain of all residues), and hydrophobic hydration (Val, Ile, Leu, Phe). In hydrophobic hydration, the configurational freedom of water molecules is reduced in the proximity of apolar residues. This ordering of water molecules results in a loss of entropy and is thus energetically unfavorable. When salt is added to the solution, the surface tension of the water increases, resulting in increased hydrophobic interaction between protein and water. The protein responds to this situation by decreasing its surface area in an attempt to minimize contact with the solvent-as manifested by folding (the folded conformation is more compact than the unfolded one) and then self-association leading to precipitation. Both folding and precipitation free up bound water, increasing the entropy of the system and making these processes energetically favorable. Timasheff and his colleagues provide a detailed discussion of these complex effects (e.g., Kita, Y. et al. 1994 *Biochemistry* 33:15178-15189; Timasheff, S. N. and Arakawa, T. 1997 in *Protein Structure: A Practical Approach,* 2nd ed (T. E. Creighton, ed.) pp. 349-364, IRL Press at Oxford University Press, Oxford).

It should be mentioned that the increase in surface tension of water by salt follows the well-known Hofmeister series, shown below (see, Parsegian, V. A. 1995 *Nature* 378:335-336, and references therein). Hence, as an approximation, those salts that favor salting-out raise the surface tension of water the highest. As $(NH_4)_2SO_4$ has a much higher solubility than any of the phosphate salts, it is the reagent of choice for salting-out. Some examples of the Hofmeister series of anions and cations are:

← increasing precipitation (salting-out)

ANIONS: $PO_4^{3-}$>$SO_4^{2-}$>$CH_3COO^-$>$Cl^-$>$Br^-$
>$ClO_4^-$>$SCN^-$

CATIONS: $NH_4^+$>$Rb^+$>$K^+$>$Na^+$>$Li^+$>$Mg^{2+}$>$Ca^{2+}$
>$Ba^{2+}$ increasing chaotropic effect (salting-in)→

Examples include ammonium phosphate, rubidium phosphate, rubidium sulfate, ammonium acetate, potassium sulfate, potassium phosphate and potassium acetate.

Ammonium sulfate fractionation is generally employed as the initial step in the isolation of crude antibodies from serum or ascitic fluid. Ammonium sulfate precipitation, in many instances, is still the method of choice because it offers a number of advantages. Ammonium sulfate fractionation provides a rapid and inexpensive method for concentrating large starting volumes. "Salting out" of polypeptides occurs at high salt concentrations where the salt competes with the polar side chains of the protein for ion pairing with the water molecules, and where the salt reduces the effective volume of solvent. As expected from these observations, the amount of ammonium sulfate required to precipitate a given protein will depend mainly on the surface charge, the surface distribution of polar side chains, and the size of the polypeptide, as well as the pH and temperature of the solution.

Immunoglobulins precipitate at 40-50% ammonium sulfate saturation depending somewhat on the species and subclass. The desired saturation is brought about either by addition of solid ammonium sulfate or by addition of a saturated solution. Although the use of solid salt reduces the final volume, this method has a number of disadvantages. Prolonged stirring, required to solubilize the salt, can lead to denaturation of proteins in the solution at the surface/air interface. Localized high concentrations of the ammonium sulfate salt may cause unwanted proteins to precipitate. Since ammonium sulfate is slightly acidic in solution, the pH of the protein solution requires constant monitoring and adjustment if solid salt is added. Therefore, it is advisable to add a buffered solution of saturated ammonium sulfate. A saturated ammonium sulfate solution is considered to be 100%, and for most antibody purification purposes, serum or ascites are mixed with an equal volume of saturated ammonium sulfate to give a 50% solution. Tables for determining amounts of solid or saturated solution to be added to achieve a desired percentage of saturation or molarity can be found in most biochemical handbooks. The density of a saturated ammonium sulfate solution at 20° C. is 1.235 g/cm$^3$. This is sufficiently low to allow removal of precipitated proteins by centrifugation.

Ammonium sulfate has been found to stabilize proteins in solution by raising the midpoint temperature at which proteins can be unfolded. This effect is thought to be the result of the interaction of the salt with the structure of water. Precipitated immunoglobulins can therefore be solubilized in a minimal volume of buffer and stored for extended periods without significant loss of bind ability or proteolytic degradation. Complete precipitation occurs within 3-8 h at 4° C. The precipitate is then collected by centrifugation, solubilized in an appropriate volume of buffer for storage at −80° C., or dialyzed to remove residual salt.

For protein purification, often two precipitation steps are carried out on a given protein sample. The first step is performed at an ammonium sulfate concentration below that required to precipitate the protein(s) of interest. Accordingly the protein(s) of interest remain in the supernatant while other proteins precipitate and are collected in the pellet upon centrifugation. The second step is performed at an ammonium sulfate concentration high enough to precipitate or pellet the protein(s) of interest. Additional proteins may remain in the supernatant.

The concentration of ammonium sulfate required for precipitation varies from protein to protein and should be determined empirically. Typically, ammonium sulfate is used in a series of steps performed at 2 to 8° C. For example, ammonium sulfate is added in increments to a concentration of 20% of saturation while gently stirring and allowed to dissolve and equilibrate between additions. Any precipitate is removed and discarded. This step typically yields macromolecules such as ribosomes, membrane fragments and even denatured proteins. This precipitation is then followed by increasing the ammonium sulfate concentration to 50% of saturation, in which the protein of interest is "salted-out" and collected via centrifugation. The remaining supernatant may contain additional "contaminating" proteins, which are then discarded. The collected precipitate can be resuspended in the minimal volume of buffer suitable for the next step in the purification process, typically via dialysis. Thus concentration, purification and buffer exchange are performed in one process.

Sodium chloride can also be utilized in a similar fashion as ammonium sulfate but with lower yield and typically an increase in denaturation of proteins. In addition, magnesium sulfate, potassium or sodium phosphate, potassium or sodium acetate and other sulfate and phosphate salts can be used with varying success.

Haptens

The invention involves the use of multivalent haptens to form immunoglobulin aggregates and monovalent haptens to dissociate multivalent haptens from the immunoglobulin aggregates. In the antigen-antibody binding reaction, the antibody-binding site is often unable to accommodate the entire antigen. The part of the antigen that is the target of antibody binding is called an antigenic determinant, and there may be one or more antigenic determinants per molecule. Small functional groups that correspond to a single antigenic determinant are called haptens. For example, these may be organic compounds, such as trinitrophenyl (TNP) or benzene arsonate, a mono- or oligosaccharide such as glucose or lactose, or an oligopeptide such as pentalysine. Antibodies specific for hapten can be studied by equilibrium dialysis using pure hapten (without carrier) or by immunoprecipitation using hapten coupled to a different (and non-cross-reacting) carrier, or by inhibition of precipitation with free hapten.

Comparative binding studies of haptens have been able to demonstrate antibody specificity despite the marked heterogeneity of antibodies. Unlike the antibodies against a multi-determinant antigen, the population of antibodies specific for a single hapten determinant is a relatively restricted population, due to the shared structural constraints necessary for hapten to fit within the antibody-combining site. When studying the cross-reactions of hapten analogs, some haptens bind all antibodies, but with reduced $K_A$. Other hapten analogs reach a plateau of binding because they fit some antibody-combining sites quite well but not others. Antibodies raised in different animals may show different cross-reactivities with related haptens. Even within a single animal, antibody affinity and specificity are known to increase over time after immunization under certain conditions. Thus, any statements about the cross-reactivity of two haptens reflect both structural differences between the haptens that affect antigen-antibody fit and the diversity of antibody-binding sites present in a given antiserum.

Haptens with binding specificity for the antibodies of interest may be purchased or synthesized. For example, peptides are synthesized conveniently on an automated peptide synthesizer using a solid-phase support and standard techniques of repetitive orthogonal deprotection and coupling. Methods of synthesizing amino acid-based polymers and glycosylated peptides are described in Sanda and Endo 1999 *Macromol Chem Phys* 200:2651-2661 and in Sears and Wong 2001 *Science* 291:2344-2350.

Multivalent Haptens

The multivalent haptens of the invention may be bivalent, trivalent, tetravalent, pentavalent, hexavalent, etc. Thus, any antibody-multivalent hapten complex can be used to purify bivalent antibodies.

The multivalent haptens are connected by a linker having a length sufficient to prevent binding of two haptens of the ligand to the same antibody. The range of linker lengths that meets these criteria will vary for different haptens and for different antibodies and can be determined empirically by those of skill in the art. For example, a multivalent hapten with an optimal linker length will assemble the largest amount of aggregate (e.g., dimer). In contrast, a shorter than optimal linker may form less aggregate dimer due to steric hindrance between antibodies, while a linker that is too long may favor the formation of monomer due to multivalent hapten binding to both antigen binding sites on the same antibody molecule.

Linker Length

With trivalent hapten, the longest distance between two hapten molecules can vary from 0.6 nm to 18 nm.

The bivalent system has less tolerance to linker length and the complexes start to dissociate (as a result of the bivalent ligand bridging the Fab binding sites on a single antibody) as the linker extends beyond 10 nm. The shortest linker we have used separating the hapten molecules is 0.6 nm long. The shortest linker we used in this study was 2.8 nm.

Dissociation Constant for Antibody-Hapten Binding $K_d^{affinity}$ for the interaction between the monovalent hapten and the IgG was 8 nM for DNP and 0.5 µM for 4-NP.

Principles of Conjugation

I. Functional Targets

The multivalent haptens of the invention are synthesized using modification and conjugation techniques. Modification and conjugation techniques are dependent on two interrelated chemical reactions: the reactive functional groups present on the various cross-linking or derivatizing reagents and the functional groups present on the target macromolecules to be modified. Without both types of functional groups being available and chemically compatible, the process of derivatization would be impossible. Reactive functional groups on cross-linking reagents, tags, and probes provide the means to label specifically certain target groups on ligands, peptides, proteins, carbohydrates, lipids, synthetic polymers, nucleic acids, and oligonucleotides. Knowledge of the basic mechanisms by which the reactive groups couple to target functional groups provides the means to design intelligently a modification or conjugation strategy. Choosing the correct reagent systems that can react with the chemical groups available on target molecules forms the basis for successful chemical modification.

The process of designing a derivatization scheme that works well in a given application is not as difficult as it may seem at first glance. A basic understanding of about a dozen reactive functional groups that are commonly present on modification and cross-linking reagents combined with knowledge of about half that many functional target groups can provide the minimum skills necessary to plan a successful experiment.

Fortunately, the principal reactive functional groups commonly encountered on bioconjugate reagents are now present on scores of commercially obtainable compounds. The resource that this arsenal of reagents provides can assist in solving almost any conceivable modification or conjugation problem. The following sections describe the predominant targets for these reagent systems. The functional groups discussed are found on virtually every conceivable biological molecule, including amino acids, peptides, proteins, sugars, carbohydrates, polysaccharides, nucleic acids, oligonucleotides, lipids, and complex organic compounds. A careful understanding of target molecule structure and reactivity provides the foundation for the successful use of all of the modification and conjugation techniques discussed in this disclosure.

A. Modification of Amino Acids, Peptides, and Proteins

Some haptens include amino acids, peptides or proteins that can be incorporated into the multivalent haptens of the invention. Protein molecules are perhaps the most common targets for modification or conjugation techniques. As the mediators of specific activities and functions within living organisms, proteins can be used in vitro and in vivo to effect certain tasks. Having enough of a protein that can bind a particular target molecule can result in a way to detect or assay the target, providing the protein can be followed or measured. If such a protein does not possess an easily detectable component, it often can be modified to contain a chemical or biological tracer to allow detectability. This type of protein complex can be designed to retain its ability to bind its natural target, while the tracer portion can provide the means to find and measure the location and amount of target molecules.

Detection, assay, tracking, or targeting of biological molecules by using the appropriately modified proteins are the main areas of application for modification and conjugation systems. The ability to produce a labeled protein having specificity for another molecule provides the key component for much of biological research, clinical diagnostics, and human therapeutics.

In this section, the structure, function, and reactivity of amino acids, peptides, and proteins will be discussed with the goal of providing a foundation of successful derivatization. The interplay of amino acid functional groups and the three-dimensional folding of polypeptide chains will be seen as forming the basis for protein activity. Understanding how the attachment of foreign molecules can affect this tenuous relationship, and thus alter protein function, ultimately will create a rational approach to protein chemistry and modification.

1. Protein Structure Reactivity

Peptides and proteins are composed of amino acids polymerized together through the formation of peptide (amide) bonds. The peptide bonded polymer that forms the backbone of polypeptide structure is called the α-chain. The peptide bonds of the α-chain are rigid planar units formed by the reaction of the α-amino group of one amino acid with the α-carboxyl group of another. The peptide bond possesses no rotational freedom due to the partial double bond character of the carbonyl-amino amide bond. The bonds around the α-carbon atom, however, are true single bonds with considerable freedom of movement.

The sequence and properties of the amino acid constituents determine protein structure, reactivity, and function. Each amino acid is composed of an amino group and a carboxyl group bound to a central carbon, termed the α-carbon. Also bound to the α-carbon is a hydrogen atom and a side chain unique to each amino acid. There are 20 common amino acids found throughout nature, each containing an identifying side chain of particular chemical structure, charge, hydrogen bonding capability, hydrophilicity (or hydrophobicity), and reactivity. The side chains do not participate in polypeptide formation and are thus free to interact and react with their environment.

Amino acids may be grouped by type depending on the characteristics of their side chains. There are seven amino acids that contain aliphatic side chains that are relatively nonpolar and hydrophobic: glycine, alanine, valine, leucine, isoleucine, methionine, and proline. Glycine is the simplest amino acid-its side chain consisting of only a hydrogen atom. Alanine is next in line, possessing just a single methyl group for its side chain. Valine, leucine, and isoleucine are slightly more complex with three or four carbon branched-chain constituents. Methionine is unique in that it is the only reactive aliphatic amino acid, containing a thioether group at the terminus of its hydrocarbon chain. Proline is actually the only imino acid. Its side chain forms a pyrrolidine ring structure with its a-amino group. Thus, it is the only amino acid containing a secondary a-amine. Due to its unique structure, proline often causes severe turns in a polypeptide chain. Proteins rich in proline, such as collagen, have tightly formed structures of high density. Collagen also contains a rare derivative of proline, 4-hydroxyproline, found in only a few other proteins. Proline, however, cannot be accommodated in normal a-helical structures, except at the ends where it may create the turning point for the chain. Poly-proline a-helical structures have been formed, but the structural characteristics of these artificial polypeptides are quite different from native protein helices.

Phenylalanine and tryptophan contain aromatic side chains that, like the aliphatic amino acids, are also relatively nonpolar and hydrophobic. Phenylalanine is unreactive toward common derivatizing reagents, whereas the indolyl ring of tryptophan is quite reactive, if accessible. The presence of tryptophan in a protein contributes more to its total absorption at 275-280 nm on a mole-per-mole basis than any other amino acid. The phenylalanine content, however, adds very little to the overall absorbance in this range.

All of the aliphatic and aromatic hydrophobic residues often are located at the interior of protein molecules or in areas that interact with other nonpolar structures such as lipids. They usually form the hydrophobic core of proteins and are not readily accessible to water or other hydrophilic molecules.

There is another group of amino acids that contains relatively polar constituents and is thus hydrophilic in character. Asparagine, glutamine, threonine, and serine are usually found in hydrophilic regions of a protein molecule, especially at or near the surface where they can be hydrated with the surrounding aqueous environment. Asparagine, threonine, and serine often are found post-translationally modified with carbohydrate in N-glycosidic (Asp) and O-glycosidic linkages (Thr and Ser). Although these side chains are enzymatically derivatized in nature, the hydroxyl and amide portions have relatively the same nucleophilicity as that of water and are therefore difficult to modify with common reagent systems under aqueous conditions.

The most significant amino acids for modification and conjugation purposes are the ones containing ionizable side chains: aspartic acid, glutamic acid, lysine, arginine, cysteine, histidine, and tyrosine. In their unprotonated state, each of these side chains can be a potent nucleophile to engage in addition reactions.

Both aspartic and glutamic acids contain carboxylate groups that have ionization properties similar to those of the C-terminal α-carboxylate. The theoretical $pK_a$ of the β-carboxyl of aspartic acid (3.7-4.0) and the γ-carboxyl of glutamic acid (4.2-4.5) are somewhat higher than the a-carboxyl groups at the C-terminal of a polypeptide chain (2.1-2.4). At pH values above their $pK_a$, these groups are generally ionized to negatively charged carboxylates. Thus at physiological pH, they contribute to the overall negative charge contribution of an intact protein.

Carboxylate groups in proteins may be derivatized through the use of amide bond forming agents or through active ester or reactive carbonyl intermediates. The carboxylate actually becomes the acylating agent to the modifying group. Amine containing nucleophiles can couple to an activated carboxylate to give amide derivatives. Hydrazide compounds react in a manner similar to that of amines. Sulfhydryls, while reactive and resulting in a thioester linkage, form unstable derivatives that hydrolyze in aqueous solutions.

Lysine, arginine, and histidine have ionizable amine containing side chains that, along with the N-terminal α-amine, contribute to a protein's overall net positive charge. Lysine contains a straight four-carbon chain terminating in a primary amine group. The ϵ-amine of lysine differs in $pK_a$ from the primary α-amines by having a slightly higher ionization point ($pK_a$ of 9.3-9.5 for lysine versus $pK_a$ of 7.6-8.0 for α-amines). At pH values lower than the $pK_a$ of these groups, the amines are generally protonated and possess a positive charge. At pH values greater than the $pK_a$, the amines are unprotonated and contribute no net charge. Arginine contains a strongly basic chemical constituent on its side chain called a guanidino group. The ionization point of this residue is so high ($pK_a > 12.0$) that it is virtually always protonated and carries a positive charge. Histidine's side chain is an imidazole ring that is potentially protonated at slightly acidic pH values ($pK_a$ 6.7-7.1). Thus, at physiological pH, these residues contribute to the overall net positive charge of an intact protein molecule. The amine-containing side chains in lysine, arginine, and histidine typically are exposed on the surface of proteins and can be derivatized with ease. The most important reactions that can occur with these residues are alkylation and acylation. In alkylation, an active alkyl group is transferred to the amine nucelophile with loss of one hydrogen. In acylation, an active carbonyl group undergoes addition to the amine. Alkylating reagents are highly varied and the reaction with an amine nucleophile is difficult to generalize. Acylating reagents, however, usually proceed through a carbonyl addition mechanism. The imidazole ring of histidine also is an important reactive species in electrophilic reactions, such as in iodination using radioactive $^{125}I$ or $^{131}I$.

Cysteine is the only amino acid containing a sulfhydryl group. At physiological pH, this residue is normally protonated and possesses no charge. Ionization only occurs at high pH ($pK_a$ 8.8-9.1) and results in a negatively charged thiolate residue. The most important reaction of cysteine groups in proteins is the formation of disulfide crosslinks with another cysteine molecule. Cysteine disulfides (called cystine residues) often are key points in stabilizing protein structure and conformation. They frequently occur between polypeptide subunits, creating a covalent linkage to hold two chains together. Cysteine and cystine groups are relatively hydrophobic and usually can be found within the core of a protein. For this reason, it is often difficult to reduce fully the disulfides of large proteins without a deforming agent present to open up the inner structure and make them accessible.

Cysteine sulfhydryls and cystine disulfides may undergo a variety of reactions, including alkylation to form stable thioether derivatives, acylation to form relatively unstable thioesters, and a number of oxidation and reduction processes. Derivatization of the side chain sulfhydryl of cysteine is one of the most important reactions of modification and conjugation techniques for proteins.

Tyrosine contains a phenolic side chain with a $pK_a$ of about 9.7-10.1. Due to its aromatic character, tyrosine is second only to tryptophan in contributing to a protein's overall absorptivity at 275-280 nm. Although the amino acid is only sparingly soluble in water, the ionizable nature of the phenolic group makes it often appear in hydrophilic regions of a protein-usually at or near the surface. Thus tyrosine derivatization proceeds without much need for deforming agents to further open protein structure. Tyrosine may be targeted specifically for modification through its phenolate anion by acylation, through electrophilic reactions such as the addition of iodine or diazonium ions, and by Mannich condensation reactions. The electrophilic substitution reactions on tyrosine's ring all occur at the ortho position to the —OH group. Most of these reactions proceed effectively only when tyrosine's ring is ionized to the phenolate anion form.

In summary, protein molecules may contain up to nine amino acids that are readily derivatizable at their side chains: aspartic acid, glutamic acid, lysine, arginine, cysteine, histidine, tyrosine, methionine, and tryptophan. These nine residues contain eight principal functional groups with sufficient reactivity for modification reactions: primary amines, carboxylates, sulfhydryls (or disulfides), thioethers, imidazolyls, guanidinyl groups, and phenolic and indolyl rings. All of these side chain functional groups in addition to the N-terminal $\alpha$-amino and the C-terminal $\alpha$-carboxylate form the full complement of polypeptide reactivity within proteins.

2. Protein Cross-linking Methods

The cross-linking of two proteins using a simple homobifunctional reagent potentially can result in a broad range of conjugates being produced. The reagent initially may react with either one of the proteins, forming an active intermediate. This activated protein may then form cross-links with the other protein or with another molecule of the same protein. The activated protein also may react intramolecularly with other functional groups on part of its own polypeptide chain. Other cross-linking molecules may continue to react with these conjugated species to form various mixed products, including severely polymerized proteins that may fall out of solution.

The problems of indeterminate conjugation products are amplified in single-step reaction procedures using homobifunctional reagents. Single-step procedures involve the addition of all reagents at the same time to the reaction mixture. This technique provides the least control over the cross-linking process and invariably leads to a multitude of products, only a small percentage of which represent the desired or optimal conjugate. Excessive conjugation may cause the formation of insoluble complexes that consist of very high molecular weight polymers. For example, one-step glutaraldehyde conjugation of antibodies and enzymes often results in significant oligomers and precipitated conjugates. To overcome this shortcoming, multistep reaction procedures have been developed using both homobifunctional and heterobifunctional reagents. Controlled, multistep conjugation protocols alleviate the polymerization problem and form relatively low molecular weight, soluble antibody-enzyme complexes.

In two-step protocols, one of the proteins to be conjugated is reacted or "activated" with a cross-linking agent and excess reagent and by-products are removed. In the second stage, the activated protein is mixed with the other protein or molecule to be conjugated, and the final conjugation process occurs.

The use of homobifunctional reagents in two-step protocols still creates many of the problems associated with single-step procedures, because the first protein can crosslink and polymerize with itself long before the second protein is added. Homobifunctional reagents by definition have the same reactive group on either end of the crosslinking molecule. Since the protein to be activated has target functional groups on every molecule that can couple with the reactive groups on the cross-linker, both ends of the reagent potentially can react. This inherent potential to polymerize uncontrollably unfortunately is characteristic of all homo bifunctional reagents, even in multistep protocols.

The greatest degree of control in cross-linking procedures is afforded using heterobifunctional reagents. Since a heterobifunctional cross-linker has different reactive groups on either end of the molecule, each side can be specifically directed toward different functional groups on proteins. Using a multistep conjugation protocol with a heterobifunctional reagent can allow one macromolecule to be activated, excess cross-linker removed, and then a second macromolecule added to induce the final linkage. Directed conjugation will occur as long as the first protein activated does not have groups able to couple with the second end of the cross-linker, whereas the second molecule does possess the correct functionalities.

Occasionally, the second protein does not naturally have the target groups necessary to couple with the second end of the cross-linker. In such cases, a specific functional group usually can be created to make the conjugation successful. In such three-step systems, the first protein is activated with the heterobifunctional reagent and purified away from excess cross-linker. The second protein is then modified to contain the specific target groups required for the second stage of the conjugation. Finally in step three, the two modified proteins are mixed to cause the coupling reaction to happen.

Two- and three-step protocols using heterobifunctional cross-linkers often are designed around amine-reactive and sulfhydryl-reactive chemical reactions. Many of these reagents utilize NHS esters on one end for coupling to amine groups on the first protein and maleimide groups on the other end that can react with sulfhydryls on the second protein. The NHS ester end is reacted with the first protein to be conjugated, forming an activated intermediate containing reactive maleimide groups. Fortunately, the maleimide end of such cross-linkers is relatively stable to degradation; thus the activated protein can be isolated without loss of sulfhydryl coupling ability. Additionally, if the second protein does not contain indigenous sulfhydryls, these can be created by an abundance of methods. After mixing the maleimide-activated protein with the sulfhydryl-containing protein, conjugation can occur only in one direction.

Control of the products of conjugation increases as the protocols progress from single step to multistep. Likewise, control of the chemistry of conjugation increases as the reagent systems evolve from simple homo bifunctional to site-directed heterobifunctional. It may appear to be a paradox, but as the method of conjugation gets more complex the result is less potential for side reactions and therefore fewer products being formed. Therefore, multistep processes using advanced heterobifunctional reagents are the best combination to ensure that the protein conjugate formed is indeed the one desired.

B. Modification of Sugars, Polysaccharides and Glycoconjugates

Some haptens include sugars, polysaccharides or glycoconjugates that can be incorporated into the multivalent haptens of the invention. Carbohydrates are characterized by the presence of polyhydroxylic aldehyde or polyhydroxylic ketone structures or polymers of such units. Sugars and polysaccharides have definite three-dimensional structures that are important for many biological functions. They are hydrophilic and thus easily accessible to aqueous reaction mediums. The chemistry of bioconjugation using carbohydrate molecules begins with an understanding of the building blocks of polysaccharide molecules.

1. Carbohydrate Structure and Function

Monosaccharide functional groups consist of either a ketone or an aldehyde, several hydroxyls, and the possibility of amine, carboxylate, sulfate, or phosphate groups as additional constituents. Amine-containing sugars may possess a free primary amine, but often are modified to the N-acetyl derivative, such as the N-acetylglucosamine residue of chitin. Sulfate-containing monosaccharides frequently are found in certain mucopolysaccharides, including chondroitin sulfate, dermatan sulfate, heparin sulfate, and keratin sulfate. Carboxylate-containing sugars include sialic acid as well as many aldonic, uronic, oxoaldonic, and ascorbic acid derivatives. Phosphate-containing monosaccharides are almost exclusively created in metabolic processes involving energy utilization, such as in the production of glucose 1-phosphate formed during glycogen breakdown and glucose 6-phosphate produced during glycolysis. Perhaps the most common phosphate sugar derivative, however, is the 5'-phosphate of D-ribose or D-2-deoxyribose found as a repeating component of RNA and DNA, respectively.

Modification and conjugation reactions can be designed to target many of these functional groups. Sugar hydroxyl groups, for example, may be derivatized by acylating or alkylating reagents, similar to the principal reactions of primary amines. However, acylation of a hydroxyl group usually creates an unstable ester derivative that is subject to hydrolysis in aqueous solution. An exception to this is acylation by a carbonylating reagent such as carbonyldiimidazole (CDI) or N,N'-Disuccinimidyl carbonate (DSC), which can produce stable carbamate linkages after subsequent conjugation with an amine containing molecule. By contrast, alkylating reagents, such as alkyl halogen compounds typically form more stable ether bonds after reaction with hydroxyls.

Carbohydrates containing hydroxyl groups on adjacent carbon atoms may be treated with sodium periodate to cleave the associated carbon-carbon bond and oxidize the hydroxyls to reactive formyl groups. Modulating the concentration of sodium periodate can direct this oxidation to modify exclusively sialic acid groups (using 1 mM concentration) or to convert all available diols to aldehydes (using 10 mM or greater concentrations). Specific monosaccharide residues may be targeted with selective sugar oxidases to generate similar aldehyde functions only on discrete points of a polysaccharide chain. The creation of formyl groups in this manner may be done on purified polysaccharide molecules, as in the case of soluble dextrans, or may be selectively performed on carbohydrate constituents of glycoproteins and other glycoconjugates. Once formed, aldehyde groups may be covalently coupled with amine-containing molecules by reductive amination using sodium cyanoborohydride.

The native reducing ends of carbohydrates also may be conjugated to amine-containing molecules by reductive amination. The reaction, however, typically is less efficient than using periodate-created aldehydes, since the open structure is in low concentration in aqueous solutions compared to the cyclic hemiacetal form. The reaction is usually allowed to continue for a week or more to reach good yields of coupling. Proteins may be modified to contain carbohydrate using this procedure.

The reducing ends of oligosaccharides can be modified with β-(p-aminophenyl)ethylamine to yield terminal arylamine derivatives. The aromatic armines then can be diazotized for coupling to active hydrogen-containing molecules, such as the tyrosine phenolic residues in proteins. Alternatively, the arylamines may be transformed into isothiocyanate derivatives for coupling to amine-containing molecules, such as proteins. The aromatic amine also may be used to conjugate the modified oligosaccharide directly with amine-reactive cross-linking agents or probes.

Another potential reaction of created or native aldehyde groups on carbohydrates is with hydrazide functionalities to form hydrazone linkages. Hydrazide-containing probes or cross-linking reagents may be conjugated with periodate-oxidized polysaccharides or with the reducing ends of sugars. The hydrazone bonds may be reduced with sodium cyanoborohydride to more stable linkages. The reduction step is recommended for long-term stability of cross-linked molecules. An example of this modification strategy is the use of biotin-hydrazide to label specifically glycoproteins at their carbohydrate locations.

Reducing sugars can be detected by reaction with phenylhydrazine to yield a hydrazone product, except that the result of the reaction is not what one might imagine giving the structure of aldoses and ketoses. Glucose, for example, can react with phenylhydrazine to yield the anticipated 1-phenylhydrazone derivative. In an excess of phenylhydrazine, however, the reaction continues to yield a 1,2-phenylhydrazone product, called an osazone, with concomitant production of aniline and ammonia. Exactly how the No. 2 hydroxyl group gets oxidized to react with another molecule of phenylhydrazine is not entirely clear, but it probably proceeds through an enol intermediate. This reaction is typical of all a-hydroxy aldehydes and a-hydroxy ketones, not just those occurring in carbohydrate molecules. Thus, glucose, mannose, and fructose all yield the same osazone product upon reaction with phenylhydrazine, since the stereochemical differences about carbons 1 and 2 are eliminated. Reversal of the phenylhydrazone linkage with an excess of benzaldehyde yields an osone, a 1-aldehyde-2-keto-derivative of the sugar. Many simple hydrazide-containing reagents probably are capable of forming similar 1,2-hydrazone derivatives with reducing sugars, provided their size does not cause steric difficulties.

Polysaccharides, glycoproteins, and other glycoconjugates therefore may be specifically labeled on their carbohydrate by creating aldehyde functional groups and subsequently derivatizing them with another molecule containing an amine or a hydrazide group. This route of derivatization is probably the most common way of modifying carbohydrates.

The hydroxyl residues of polysaccharides also may be activated by certain compounds that form intermediate reactive derivatives containing good leaving groups for nucleophilic substitution. Reaction of these activated hydroxyls with nucleophiles such as amines results in stable covalent bonds between the carbohydrate and the amine-containing molecule. Activating agents that can be employed for this purpose include carbonyl diimidazole, certain chloroformate derivatives, tresyl- and tosyl chloride, cyanogen bromide, divinylsulfone, cyanuric chloride, disuccinimidyl carbonate, and various bis-epoxide compounds. Such activation steps are frequently done in nonaqueous solutions (i.e., dry dioxane, acetone, Dimethylformamide (DMF), or Dimethylsulfoxide (DMSO)) to prevent hydrolysis of the active species. Although many pure polysaccharides can tolerate these organic environments, many biological glycoconjugates cannot. Thus, these methods are suitable for activating pure polysaccharides such as dextran, cellulose, agarose, and other carbohydrates, but are not appropriate for modifying sugar residues on glycoproteins. Many of these hydroxyl-activating reagents also can be used to activate polysaccharide chromatography supports and other hydroxyl-containing synthetic polymers such as polyethylene glycol.

The hydroxyl groups of carbohydrate molecules are only mildly nucleophilic approximately equal to water in their relative nucleophilicity. Since the majority of reactive functional groups on bioconjugation reagents are dependent on nucleophilic reactions to initiate covalent bond formation, specific hydroxyl group modification is usually not possible in aqueous solution. Hydrolysis of the active groups on crosslinking reagents occurs faster than hydroxyl group modification, due to the relative high abundance of water molecules compared to the amount of carbohydrate hydroxyls present. In some cases, even if modification does occur, the resultant bond may be unstable. For instance, N-hydroxysuccinimide (NHS) esters can react with hydroxyls to form ester linkages, which are themselves unstable to hydrolysis.

Anhydrides, such as acetic anhydride, may react with carbohydrate hydroxyls even in aqueous environments to form acyl derivatives. The reaction, however, is reversible by incubation with hydroxylamine at pH 10-11.

Epoxide-containing reagents, such as the homobifunctional 1,4-(butanediol) diglycidyl ether, can react with polysaccharide hydroxyl groups to form stable ether bonds. Bis-epoxy compounds have been used to couple sugars and polysaccharides to insoluble matrices for affinity chromatography. The reaction of epoxides, however, is not specific for hydroxyl groups and will cross-react with amine and sulfhydryl functional groups, if present.

Hydroxyl groups on carbohydrates may be modified with chloroacetic acid to produce a carboxylate functional group for further conjugation purposes. In addition, indigenous carboxylate groups, such as those in sialic acid residues and aldonic or uronic acid-containing polysaccharides, may be targeted for modification using typical carboxylate modification reactions. However, when these polysaccharides are part of macromolecules containing other carboxylic acid groups such as glycoproteins, the targeting will not be specific for the carbohydrate alone. Pure polysaccharides containing carboxylate groups may be coupled to amine-containing molecules by use of the carbodiimide reaction. The carboxylate is activated to an O-acylisourea intermediate which is in turn attacked by the amine compound. The result is the formation of a stable amide linkage with loss of one molecule of isourea.

Carbohydrate molecules containing amine groups, such as D-glucosamine, may be easily conjugated to other macromolecules using a number of amine-reactive chemical reactions and cross-linkers. Some polysaccharides containing acetylated amine residues, such as chitin which contains N-acetylglucosamine, may be deacetylated under alkaline conditions to free the amines (forming chitosan in this case).

Amine functional groups also may be created on polysaccharides. The reducing ends of carbohydrate molecules (or generated aldehydes) may be reacted with small diamine compounds to yield short alkylamine spacers that can be used for subsequent conjugation reactions. Hydrazide groups may be similarly created using bis-hydrazide compounds.

Phosphate-containing carbohydrates that are stable, such as the 5'-phosphate of the ribose derivatives of oligonucleotides, may be targeted for modification using a carbodiimide-facilitated reaction. The water-soluble carbodiimide EDC can react with the phosphate groups to form highly reactive phospho-ester intermediates. These intermediates can react with amine- or hydrazide-containing molecules to form stable phosphoramidate bonds.

2. Carbohydrate Cross-linking Methods

The presence of carbohydrate on biomolecules provides important points of attachment for modification and conjugation reactions. Coupling only through polysaccharide chains often can direct the reaction away from active centers or critical points in protein molecules, thus preserving activity. Cross-linking strategies involving polysaccharides or glycoconjugates usually involve a two- or three-step reaction sequence. If no reactive functional groups other than hydroxyl groups are present on the carbohydrate, then the first step is to create sufficiently reactive groups to couple with the functional groups of a second molecule.

Perhaps the easiest way to target specifically polysaccharides on glycoproteins is through mild sodium periodate oxidation. Periodate cleaves adjacent hydroxyl groups in sugar residues to create highly reactive aldehyde functional groups. It is an aqueous reaction that is tolerated by most biological glycoconjugates and pure polysaccharide molecules. Particularly convenient is that the level of periodate addition can be adjusted to cleave selectively only certain sugars in the polysaccharide chain. A concentration of 1 mM sodium periodate specifically oxidizes sialic acid residues to aldehydes, leaving all other monosaccharides untouched. Increasing the concentration to 10 mM, however, will cause oxidation of other sugars in the carbohydrate chain, including galactose and mannose residues on glycoproteins. The generated aldehydes then can be used in coupling reactions with amine- or hydrazide containing molecules to form covalent linkages. Amines can react with formyl groups under reductive amination conditions using a suitable reducing agent such as sodium cyanoborohydride. The result of this reaction is a stable secondary amine linkage. Hydrazides spontaneously react with aldehydes to form hydrazone linkages, although the addition of a reducing agent greatly increases the efficiency of the reaction and the stability of the bond.

Oxidized glycoconjugates usually are stable enough to be stored freeze-dried without loss of activity prior to a subsequent conjugation reaction. Storage in solution, however, may cause slow polymerization if the molecule also contains amine groups, as in glycoproteins. Sometimes the protein can be treated to block its amines prior to periodate oxidation, as in the procedure often used with the enzyme horseradish peroxidase (HRP), thus eliminating the potential for self-conjugation.

If the second molecule to be coupled to the oxidized glycoconjugate already has the requisite amines or hydrazide groups, then directly mixing the two components together in the presence of a reductant is all that is needed. This is an example of a two-step procedure. However, if the second molecule possesses none of the appropriate functional groups for coupling, then modifying it to contain them must be done prior to the conjugation reaction. Thus, a three-step protocol results. The use of other functional groups (either indigenous or created) on polysaccharide molecules to effect a cross-linking reaction can be done in similar two- or three-step strategies.

Occasionally, it is important to conjugate a polysaccharide-containing molecule to another molecule while retaining, as much as possible, the carbohydrate's original chemical and three-dimensional structure. For instance, in the preparation of immunogen conjugates by coupling a polysaccharide molecule to a carrier, care should be taken to preserve the structure of the carbohydrate to ensure antibody recognition of the native molecule. In this case, periodate oxidative techniques may not be the best choice to effect cross-linking due to the potential for extensive ring opening throughout the chain. Under controlled conditions, however, where periodate is carefully used in limiting quantities, this method has proved successful in creating oligosaccharide carrier conjugates.

Retention of native carbohydrate structure also is important in applications that utilize the conjugated polysaccharide in binding studies with receptors or lectins. In these cases, the carbohydrate should be modified at limited sites, preferentially only at its reducing end.

C. Modification of Nucleic Acids and Oligonucleotides

Some haptens include nucleic acids or oligonucleotides that can be incorporated into the multivalent haptens of the invention. The nucleic acid polymers DNA and RNA form the most basic units of information storage within cells. The conversion of their unique information code into proteins and enzymes is the fundamental step in controlling all cellular processes. Targeting segments of this encoded data with labeled probes that are able to bind to specific genetic regions allows detection, localization or quantification of discrete oligonucleotides. This targeting capability is made possible by the predictable nature of nucleic acid interactions. Despite the complexity of the genetic code, the base-pairing process, which causes one oligonucleotide to bind to its complementary sequence, is rather simplistic. Nucleic acids are the only type of complex biological molecule wherein their binding properties can be fully anticipated and incorporated into synthetic oligonucleotide probes. Thus, a short DNA segment can be synthetically designed and used to target and hybridize to a complementary DNA strand within a much larger chromosome. If the small oligonucleotide is labeled with a detectable component that does not interfere in the base-pairing process, then the targeted DNA can be assayed. Bioconjugate techniques involving nucleic acids are becoming one of the most important application areas of cross-linking and modification chemistry.

1. Nucleotide Functional Groups

Chemical attachment of a detectable component to an oligonucleotide forms the basis for constructing a sensitive reagent. Unfortunately, the methods developed to cross-link or label other biological molecules such as proteins do not always apply to nucleic acids. The major reactive sites on proteins involve primary amines, sulfhydryls, carboxylates, or phenolates-groups that are relatively easy to derivatize. RNA and DNA contain none of these functional groups. They also are relatively unreactive directly with many of the common bioconjugate reagents.

However, there are particular sites that can be modified on the bases, sugars, or phosphate groups of nucleic acids to produce derivatives able to couple with a second molecule. The chemical reactions are almost entirely unique to DNA and RNA work, but once mastered, the process of conjugation can be done with the same ease as with protein molecules.

2. Polynucleotide Cross-Linking Methods

The unique properties of oligonucleotides create cross-linking options that are far different from those of any other biological molecule. Nucleic acids are the only major class of macromolecule that can be specifically synthesized in vitro by enzymatic means. The addition of modified nucleoside triphosphates to an existing DNA strand by the action of polymerases or transferases allows addition of spacer arms or detection components at random or discrete sites along the chain. Alternatively, chemical methods that modify nucleotides at selected functional groups can be used to produce spacer arm derivatives or activated intermediates for subsequent coupling to other molecules.

Large amounts of base derivatization along a polynucleotide chain has the potential for causing obstructions in a reaction.

By contrast, derivatization at the ends of an oligo or at the sugar-phosphate backbone usually produces little interference in base-pairing. Conjugates may be created by enzymatic polymerization of functionalized nucleoside triphosphates off the 3' end or by chemical modification of the 5' phosphate group with minimal to no interference in reaction potential.

D. Creating Specific Functional Groups

During synthesis of the multivalent haptens of the invention, it is often desirable to alter the native structure of a macromolecule to provide functional targets for modification or conjugation. The use of most reagent systems requires the presence of particular chemical groups to effect coupling. For instance, heterobifunctional cross-linkers may contain two different reactive species that are directed against different functional groups. One target molecule must contain chemical groups able to react with one end of the cross-linker, while the other target molecule must contain groups able to react with the other end. Occasionally, the required chemical groups are not present on one of the target molecules and must be created. This usually can be done by reacting an existing chemical group with a modification reagent that contains or produces the desired functional group upon coupling. Thus, an amine can be "changed" into a sulfhydryl or a carboxylate can be altered to yield an amine simply by using the appropriate reagent.

This same type of modification strategy also can be used to create highly reactive groups from functional groups of rather low reactivity. For instance, carbohydrate chains on glycoproteins can be modified with sodium periodate to transform their rather unreactive hydroxyl groups into highly reactive aldehydes. Similarly, cystine or disulfide residues in proteins can be selectively reduced to form active sulfhydryls, or 5' phosphate groups of DNA can be transformed to yield modifiable amines.

Alternatively, spacer arms can be introduced into a macromolecule to extend a reactive group away from its surface. The extra length of a spacer can provide less steric hindrance to conjugation and often yields more active complexes.

The use of modification reagents to create specific functional groups is an important technique to master. In one sense, the process is like using building blocks to construct on a target molecule any desired functional groups necessary for reactivity. The success of many conjugation schemes depends on the presence of the correct chemical groups. Care should be taken in choosing a modification strategy, however, since some chemical changes will radically affect the native structure and activity of a macromolecule. A protein may lose its capacity to bind a specific ligand. An enzyme may lose the ability to act upon its substrate. A DNA probe may no longer be able to hybridize to its complementary target. In many cases, the potential for inactivation relates to changing conformational structures, blocking active sites, or modifying critical functional groups. Trial and error and careful literature searches are often necessary to optimize any modification tactic.

Sulfhydryl residues can be introduced (Thiolation). For example amines can be modified with 2-Iminothiolane (Traut's Reagent), SATA, SATP, SPDP, SMPT, N-Acetylhomocysteinethiolactone, and SAMSA. Sulfhydryl residues can also be introduced by the modification of aldehydes or ketones with AMBH, by modification of carboxylates or phosphates with cystamine and the use of disulfide reductants. The Ellman's Assay may be used for the determination of sulfhydryls.

Carboxylate groups may be added. For example, amines can be modified with anhydrides, sulfhydryls can be modified with iodoacetate, and hydroxyls can be modified with chloroacetic acid.

Primary amine groups can be introduced by modification of carboxylates with diamines, modification of sulfhydryl, with N-(β-Iodoethyl)trifluoroacetamide (Aminoethyl-8), modification of sulfhydryl, with ethylenimine, modification of sulfhydryls with 2-bromoethylamine, modification of carbohydrates with diamines, modification of alkylphosphates with diamines, modification of aldehydes with ammonia or diamines, and by introduction of arylamines on phenolic compounds. The presence of amine groups can be detected using amine detection reagents.

Aldehyde residues can be introduced by periodate oxidation of glycols and carbohydrates, oxidase modification of sugar residues, modification of amines with NHS-aldehydes (SFB and SFPA), and modification of amines with glutaraldehyde Hydrazide functional groups can be added by modification of aldehydes with bis-hydrazide compounds, by modification of carboxylates with bis-hydrazide compounds and by modification of alkylphosphates with bis-hydrazide compounds.

II. The Chemistry of Reactive Groups

Chemical modification or conjugation processes are used to synthesize the multivalent haptens of the invention. Every chemical modification or conjugation process involves the reaction of one functional group with another, resulting in the formation of a covalent bond. The creation of bioconjugate reagents with spontaneously reactive or selectively reactive functional groups forms the basis for simple and reproducible cross-linking or tagging of target molecules. Of the hundreds of reagent systems described in the literature or offered commercially, most utilize common organic chemical principles that can be reduced to a couple dozen or so primary reactions. An understanding of these basic reactions can provide insight into the properties and use of bioconjugate reagents even before they are applied to problems in the actual practice.

This section is designed to provide a general overview of activation and coupling chemistry. Some of the reagents discussed in this part are not themselves cross-linking or modification compounds, but may be used to form active intermediates with another functional group. These active intermediates subsequently can be coupled to a second molecule that possesses the correct chemical constituents that allow bond formation to occur.

The multivalent haptens of the invention may be conjugated to a cross-linker by an amine-reactive chemical reaction. Amine-Reactive Chemical Reactions include the use of isothiocyanates, isocyanates, Acyl Azides, NHS Esters, Sulfonyl Chlorides, Aldehydes and Glyoxals, Epoxides and Oxiranes, Carbonates, Arylating Agents, Imidoesters, Carbodiimides, and Anhydrides.

The multivalent haptens of the invention may be conjugated to a cross-linker by a thiol-reactive chemical reaction. Thiol-Reactive Chemical Reactions may be performed with Haloacetyl and Alkyl Halide Derivatives, Maleimides, Aziridines, Acryloyl Derivatives, Arylating Agents, Thiol-Disulfide Exchange Reagents (e.g., Pyridyl Disulfides, TNB-Thiol, and Disulfide Reductants).

The multivalent haptens of the invention may be conjugated to a cross-linker by a carboxylate-reactive chemical reaction. Carboxylate-Reactive Chemical Reactions can be done with Diazoalkanes and Diazoacetyl Compounds, Carbonyldiimidazole and Carbodiimides.

The multivalent haptens of the invention may be conjugated to a cross-linker by a hydroxyl-reactive chemical reaction. Hydroxyl-Reactive Chemical Reactions can be done with Epoxides and Oxiranes, Carbonyldiimidazole, N,N'-Disuccinimidyl carbonate or N-Hydroxysuccinimidyl chloroformate. They can be performed by Oxidation or with Periodate and Enzymatic Oxidation. In addition, Hydroxyl-Reactive Chemical Reactions can by done using Alkyl Halogens and Isocyanates.

The multivalent haptens of the invention may be conjugated to a cross-linker by an aldehyde- or ketone-reactive chemical reaction. Aldehyde- and Ketone-Reactive Chemical Reactions can be done with Hydrazine derivatives, Schiff Base Formation, Reductive Amination and Mannich Condensation.

The multivalent haptens of the invention may be conjugated to a cross-linker by an active hydrogen-reactive chemical reaction. Active Hydrogen-Reactive Chemical Reactions can be done using Diazonium Derivatives, Mannich Condensation and Iodination Reactions.

The multivalent haptens of the invention may be conjugated to a cross-linker by a photoreactive chemical reaction. Photoreactive Chemical Reactions include the use of Aryl Azides and Halogenated Aryl Azides, Benzophenones, certain Diazo Compounds, and Diazirine Derivatives.

III. Bioconjugate Reagents

A. Zero-Length Cross-Linkers

In some cases, the multivalent haptens of the invention may be synthesized using zero-length cross-linkers. The smallest available reagent systems for bioconjugation are the so-called zero-length cross-linkers. These compounds mediate the conjugation of two molecules by forming a bond containing no additional atoms. Thus, one atom of a molecule is covalently attached to an atom of a second molecule with no intervening linker or spacer. In many conjugation schemes, the final complex is bound together by virtue of chemical components that add foreign structures to the substances being cross-linked. In some applications, the presence of these intervening linkers may be detrimental to the intended use. For instance, in the preparation of hapten-carrier conjugates the complex is formed with the intention of generating an immune response to the attached hapten. Occasionally, a portion of the antibodies produced by this response will have specificity for the cross-linking agent used in the conjugation procedure. Zero-length cross-linking agents eliminate the potential for this type of cross-reactivity by mediating a direct linkage between two substances.

The reagents described in this section can initiate the formation of three types of bonds: an amide linkage made by the condensation of a primary amine with a carboxylic acid, a phosphoramidate linkage made by the reaction of a organic phosphate group with a primary amine, and a secondary or tertiary amine linkage made by the reductive amination of a primary or secondary amine with an aldehyde group. Therefore, using these reagent systems, substances containing amines can be conjugated with other molecules containing phosphates or carboxylates. Alternatively, substances containing amines can be cross-linked to molecules containing formyl groups. All of the reactions are quite efficient, and depending on the reagent chosen and the desired application, they may be performed in aqueous or nonaqueous environments.

Zero-Length cross-linkers include, for example, carbodiimides (e.g., EDC, EDC plus Sulfo-NHS, CMC, DCC, DIC), Woodward's Reagent K, and N,N'-Carbonykliimidazole. Schiff Base Formation and Reductive Amination can be used for conjugation with such linkers.

B. Homobifunctional Cross-Linkers

In some cases, the multivalent haptens of the invention may be synthesized using homobifunctional cross-linkers. The first cross-linking reagents used for modification and conjugation of macromolecules consisted of bi-reactive compounds containing the same functional group at both ends. Most of these homobifunctional reagents were symmetrical in design with a carbon chain spacer connecting the two identical reactive ends. Like molecular rope, these reagents could tie one protein to another by covalently reacting with the same common groups on both molecules. Thus, the lysine ε-amines or N-terminal amines of one protein could be cross-linked to the same functional groups on a second protein simply by mixing the two together in the presence of the homo bifunctional reagent.

The ability to link so easily two proteins or other molecules having different binding specificities or catalytic activities opened the potential for creating a new universe of unique and powerful reagent systems for use in assay and targeting applications. The variety and reactivity of homo bifunctional reagents multiplied dramatically throughout the 1970s and 1980s. Today, there are dozens of commercially available crosslinkers possessing almost every length and reactivity desired.

The main disadvantage, however, of using simple homobifunctional reagents is the potential for creating a broad range of poorly defined conjugates. When cross-linking two proteins, for example, the reagent may react initially with either one of the proteins, forming an active intermediate. This activated protein may form cross-links with the second protein or react with another molecule of the same type. It also may react intramolecularly with other functional groups on part of its own polypeptide chain. In addition, other cross-linking molecules may continue to react with these intermediates to form various mixed oligomers, including severely polymerized products that may even precipitate.

The problem of poorly defined conjugation products is exaggerated in single-step reaction procedures using homobifunctional reagents. Single-step procedures involve the addition of all reagents at the same time to the reaction mixture. This technique provides the least control over the cross-linking process and invariably leads to a multitude of products, only a small percentage of which represent the desired conjugate. Excessive conjugation may cause the formation of insoluble complexes that consist of very high molecular weight polymers. For example, one-step glutaraldehyde conjugation of antibodies and enzymes often results in significant oligomers and precipitated conjugates. To overcome this shortcoming, two-step reaction procedures have been developed using homo bifunctional reagents. Controlled, two-step conjugation protocols somewhat alleviate the polymerization problem with homo bifunctional reagents, but can never totally avoid it.

In two-step protocols, one of the proteins to be conjugated is reacted with the homodifunctional reagent and excess cross-linker and by-products are removed. In the second stage, the activated protein is mixed with the other protein or molecule to be conjugated, and the final conjugation process occurs.

One potential problem of such two-step procedures is hydrolysis of the activated intermediate before addition of the second molecule to be conjugated. For instance, NHS ester homobifunctionals hydrolyze rapidly and may degrade before the second stage of the cross-linking is initiated. In addition, the use of homobifunctional reagents in two-step protocols still produces many of the problems associated with single-step procedures, because the first protein can cross-link and polymerize with itself long before the second protein is added. Since the first protein to be activated has target functional groups on every molecule that can couple with both the reactive groups on the cross-linker, both ends of the reagent potentially can react. This inherent capacity to polymerize uncontrollably unfortunately is characteristic of all homo bifunctional reagents, even in multistep protocols.

Although their shortcomings in this regard are clearly recognized, homobifunctional reagents continue to be popular choices for all kinds of conjugation applications. The fact is, in many cross-linking functions, they work well enough to form effective conjugates. Even glutaraldehyde-mediated antibody-enzyme conjugates still are commonly utilized in everything from research to diagnostics.

The particular cross-linkers discussed in this section are the types most often referred to in the literature or are commercially available. Many other forms of homobifunctional reagents containing almost every conceivable chain length and reactivity can be found mentioned in the scientific literature.

Homo functional cross-linkers include, for example, homobifunctional NHS Esters (e.g., DSP and DTSSP, DSS and $BS^3$, DST and Sulfo-DST, BSOCOES and Sulfo-BSO-COES, EGS and Sulfo-EGS, DSG and DSC); Homobifunctional Imidoesters (e.g., DMA, DMP, DMS and DTBP), Homobifunctional Sulfhydryl-Reactive Cross-linkers (e.g., DPDPB and BMH), Difluorobenzene Derivatives (e.g., DFDNB and DFDNPS), Homobifunctional Photoreactive Cross-linkers (e.g., BASED), Homobifunctional Aldehydes (e.g., Formaldehyde and Glutaraldehyde), Bis-epoxides (e.g., 1,4-Butanediol Diglycidyl Ether), Homobifunctional Hydrazides (e.g., Adipic Acid Dihydrazide and Carbohydrazide), Bis-diazonium Derivatives (e.g., o-Tolidine, Diazotized and Bis-diazotized Benzidine) and Bis-alkylhalides.

C. Heterobifunctional Cross-Linkers

In some cases, the multivalent haptens of the invention may be synthesized using heterobifunctional cross-linkers. Heterobifunctional conjugation reagents contain two different reactive groups that can couple to two different functional targets on proteins and other macromolecules. For example, one part of a cross-linker may contain an amine-reactive group, while another portion may consist of a sulfhydryl-reactive group. The result is the ability to direct the cross-linking reaction to selected parts of target molecules, thus garnering better control over the conjugation process.

Heterobifunctional reagents can be used to cross-link proteins and other molecules in a two- or three-step process that limits the degree of polymerization often obtained using homobifunctional cross-linkers. In a typical conjugation scheme, one protein is modified with a heterobifunctional using the cross-linker's most reactive or most labile end. The modified protein is then purified from excess reagent by gel filtration or rapid dialysis. Most heterobifunctionals contain at least one reactive group that displays extended stability in aqueous environments, therefore allowing purification of an activated intermediate before adding the second molecule to be conjugated. For instance, an NHS ester-maleimide heterobifunctional can be used to react with the amine groups of one protein through its NHS ester end (the most labile functional group), while preserving the activity of its maleimide functional group. Since the maleimide group has greater stability in aqueous solution than the NHS ester group, a maleimide-activated intermediate may be created. After a quick purification step, the maleimide end of the cross-linker then can be used to conjugate to a sulfhydryl-containing molecule.

Such multi-step protocols offer greater control over the resultant size of the conjugate and the molar ratio of components within the cross-linked product. The configuration or structure of the conjugate can be regulated by the degree of initial modification of the first protein and by adjusting the amount of second protein added to the final conjugation reaction. Thus, low- or high-molecular-weight conjugates may be obtained to better fashion the product toward its intended use.

Hererobifunctional cross-linking reagents also may be used to site-direct a conjugation reaction toward particular parts of target molecules. Amines may be coupled on one molecule while sulfhydryls or carbohydrates are targeted on another molecule. Directed coupling often is important in preserving critical epitopes or active sites within macromolecules. For instance, antibodies may be coupled to other proteins while directing the cross-linking reaction away from the antigen binding sites, thus maximizing antibody activity in the conjugate.

Heterobifunctional reagents containing one photoreactive end may be used to nonselectively insert into target molecules by UV irradiation. The photoreactive group is stable until exposed to high intensity light at UV wavelengths.

The third component of all heterobifunctional reagents is the cross-bridge or spacer that ties the two reactive ends together. Cross-linkers may be selected based not only on their reactivities, but also on the length and type of cross-bridge they possess. Some heterobifunctional families differ solely in the length of their spacer. The nature of cross-bridge also may govern the overall hydrophilicity of the reagent. A number of heterobifunctionals contain cleavable groups within their cross-bridge, lending greater flexibility to the experimental design. A few cross-linkers contain peculiar crossbridge constituents that actually affect the reactivity of their functional groups. For instance, it is known that a maleimide group that has an aromatic ring immediately next to it is less stable to ring opening and loss of activity than a maleimide that has an aliphatic ring adjacent to it.

Heterobifunctional Cross-Linkers include, for example, Amine-Reactive and Sulfhydryl-Reactive Cross-linkers (e.g., SPDP, LC-SPDP, and Sulfo-LC-SPDP, SMPT and Sulfo-LC-SMPT, SMCC and Sulfo-SMCC, MBS and Sulfo-MBS, SIAB and Sulfo-SIAB, SMPB and Sulfo-SMPB, GMBS and Sulfo-GMBS, SIAX and SIAXX, SIAC and SIACX, and NPIA), Carbonyl-Reactive and Sulfhydryl-Reactive Cross-linkers (e.g., MPBH, $M_2C_2H$, and PDPH), Amine-Reactive and Photoreactive Cross-linkers (NHS-ASA, Sulfo-NHS-ASA, and Sulfo-NHS-LC-ASA, SASD, HSAB and Sulfo-HSAB, SANPAH and Sulfo-SANPAH, ANB-NOS, SAND, SADP and Sulfo-SADP, Sulfo-SAPB, SAED, Sulfo-SAMCA, p-Nitrophenyl Diazopyruvate, and PNP-DTP), Sulfhydryl-Reactive and Photoreactive Cross-linkers (e.g., ASIB, APDP, Benzophenone-4-iodoacetamide and Benzophenone-4-maleimide), Carbonyl-Reactive and Photoreactive Cross-linkers (e.g., ABH), Carboxylate-Reactive and Photoreactive Cross-linkers (e.g., ASBA), and Arginine-Reactive and Photoreactive Cross-linkers (e.g., APG).

Further Disclosure

According to the methods of the invention, cyclic immunoglobulin aggregates are formed by addition of multivalent hapten to a salt solution of soluble antibodies or antibody fragments, wherein the multivalent hapten possesses a linker between the two haptens effective to prevent the binding of both haptens of the ligand to the same antibody or antibody fragment. After the initial precipitation, the precipitate is removed from the supernatant using standard techniques known in the art such as centrifugation or filtration. In one example, precipitated material can be removed by centrifugation at 6000 rpm and 20° C. for 30 minutes using a GS3 or GSA rotor with a Sorvall RC-5B centrifuge. In another example the precipitated material can be removed by filtration (e.g., with a depth filter device from Pall Life Sciences) and optionally with a filter aid such as Celpure from Advanced Minerals Corp. Non-limiting examples of filter aids, which are inorganic mineral powders or organic fibrous materials used in combination with filtration hardware to enhance filtration performance, include diatomite, perlite, and cellulose. An example of a filter aid useful in the methods of the invention is Celpure 1000 (Advanced Minerals Corporation).

Following removal of contaminating proteins from the antibody source, multivalent hapten is added to the supernatant to induce the formation of cyclic aggregates. Additional filtration or centrifugation steps are then performed to isolate precipitated cyclic aggregates that result from the aggregation of immunoglobulins (e.g., IgGs and IgEs) with multivalent haptens.

Finally, additional steps of the invention may include dissolving pelleted cyclic immunoglobulin aggregates and dissociating them from multivalent hapten by addition of excess monovalent hapten, and removal of said monovalent haptens from the monoclonal antibodies (e.g., by microdialysis, size exclusion chromatography and Centricon® Centrifugal Filter Units manufactured by Millipore).

Microdialysis

Dialysis is a classic separation technique that facilitates the removal of small, unwanted compounds from macromolecules in solution by selective diffusion through a semi-permeable membrane. The molecular weight cut-off (MWCO) of the membrane is determined by the size of the pores. The sample and the buffer against which it is dialyzed (dialysate) are placed on opposite sides of the membrane. The volume of dialysis buffer is typically 200-500 times the volume of the sample. Differences in the composition of the sample and dialysis buffer create a concentration differential across the membrane. Molecules that are larger than the membrane pores are retained on the sample side of the membrane, but small molecules diffuse freely through the membrane and approach an equilibrium concentration with the entire dialysate volume. In this way, the concentration of contaminants in the sample can be decreased to acceptable or negligible levels.

In working with proteins and nucleic acids, it is often necessary to eliminate small molecular weight substances such as reducing agents (e.g., dithiothreitol (DTT), 2-mercaptoethanol (BME)), unreacted cross-linking or labeling reagents (sulfo-SMCC, biotin), preservatives (sodium azide, thimerosol) and monovalent hapten that might interfere with a subsequent step in the experimental procedure. Similarly, it is often required to perform a buffer exchange to transfer a protein into a more appropriate buffer prior to subsequent applications such as electrophoresis, ion exchange or affinity chromatography.

Dialysis Based on Principles of Diffusion

Dialysis is a well-established separation method that allows for buffer exchange and low molecular weight contaminant removal from sample solutions without significant loss of the macromolecule of interest. It is based on the diffusion of small molecules in a sample through a semi-permeable membrane into a second liquid or dialysate. Diffusion is a process that results from the thermal, random movement of molecules from an area of higher to one of lower concentration.

The rate of diffusion of a molecule is directly proportional to its concentration and inversely proportional to its molecular weight. The higher the concentration, the greater the probability that the molecule will come in contact with the membrane and diffuse across it to the other side. The larger the molecule, the slower its movement in solution and the less chance that it will collide with and diffuse through the membrane even if it is small enough to pass through the pores. Molecular movement and membrane permeation rate is directly proportional to temperature, which means that dialysis will proceed faster at room temperature than at 4° C. In selecting the most appropriate temperature, it is important to take into account the thermal stability of the molecule of interest.

Dialysis rate is directly proportional to the surface area of the membrane and inversely proportional to its thickness. Membranes normally used for laboratory dialysis applications range from 12-30 μm thick, providing good diffusion rate as well as structural integrity.

Selection of Membrane MWCO

Membrane pore size regulates the size of the molecules that can diffuse across it. To select the best membrane for a particular application, it is important to understand the significance of molecular weight cut off (MWCO) determinations and how they are characterized.

For actual use conditions, a membrane should be chosen with a MWCO far below that of the molecule of interest, to ensure good sample recovery, but large enough to facilitate efficient separation. A MWCO of approximately 10,000 is frequently used to remove small molecular weight contaminants from a globular protein sample. Dialysis is not intended as a method of separation for molecules of similar molecular weight. In selecting a buffer system, it is important to remember that pH can alter the size, three dimensional shape and charge of the protein, affecting its ability to pass through the pores of the membrane.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. A method of purifying bivalent antibodies or antibody fragments that are active at both Fab sites from a source of antibodies or antibody fragments using a non-chromatographic method comprising:
   (a) inducing the formation of cyclic immunoglobulin aggregates by addition of multivalent hapten to a salt solution of soluble antibodies or antibody fragments, wherein said multivalent hapten possesses a linker between the multiple haptens effective to prevent the binding of the multiple haptens to the same antibody or antibody fragment, and wherein the salt in the salt solution is present at a concentration sufficient to precipitate cyclic immunoglobulin aggregates;
   (b) recovering the cyclic immunoglobulin aggregates from the salt solution;
   (c) dissolving the cyclic immunoglobulin aggregates recovered in (b) and dissociating the cyclic immunoglobulin aggregates from the multivalent haptens by addition of excess monovalent hapten; and
   (d) separating the antibodies or antibody fragments from the monovalent and multivalent haptens.

2. The method of claim 1, further comprising
removing from the salt solution proteins having molecular masses >300 kDa by salt precipitation and recovery of antibody or antibody fragment that remains soluble prior to step (a).

3. The method of claim 1, wherein said antibodies are monoclonal antibodies.

4. The method of claim 3 wherein said monoclonal antibodies are IgGs.

5. The method of claim 3 wherein said monoclonal antibodies are IgEs.

6. The method of claim 1, wherein said antibodies are polyclonal antibodies.

7. The method of claim 1, wherein said source is ascites.

8. The method of claim 1, wherein said salt is ammonium sulfate.

9. The method of claim 1, wherein the $K_d^{affinity} \leq 10$ nM.

10. The method of claim 1, wherein the inducing step (a) is carried out in about a 35% ammonium sulfate solution.

11. The method of claim 1, wherein the multiple haptens of the multivalent hapten are the same.

12. The method of claim 1, wherein the multiple haptens of the multivalent hapten are different.

13. The method of claim 1, wherein the hapten of the monovalent hapten is the same as the hapten(s) of the multivalent hapten.

14. The method of claim 1, wherein the hapten of the monovalent hapten is different from the hapten(s) of the multivalent hapten.

15. The method of claim 1, wherein the purity of the purified antibody or antibody fragment is in the range of about 30 to about 100% pure.

16. The method of claim 1, wherein said multivalent hapten is bivalent.

17. The method of claim 16, wherein the linker length separating the hapten molecules is from 0.6 nm to 10 nm.

* * * * *